United States Patent
Tsakalakos et al.

(10) Patent No.: US 10,120,102 B2
(45) Date of Patent: Nov. 6, 2018

(54) FLUID SENSOR CABLE ASSEMBLY, SYSTEM, AND METHOD

(71) Applicant: General Electric Company, Schenectady, NY (US)

(72) Inventors: Loucas Tsakalakos, Niskayuna, NY (US); Slawomir Rubinsztajn, Niskayuna, NY (US); Renato Guida, Niskayuna, NY (US); Mahadevan Balasubramaniam, Niskayuna, NY (US); Boon Kwee Lee, Niskayuna, NY (US); Brian Magann Rush, Niskayuna, NY (US); Faisal Razi Ahmad, Niskayuna, NY (US); Sudeep Mandal, Niskayuna, NY (US); David Sirda Shanks, Aberdeen (GB)

(73) Assignee: General Electric Company, Schenectady, NY (US)

( * ) Notice: Subject to any disclaimer, the term of this patent is extended or adjusted under 35 U.S.C. 154(b) by 217 days.

(21) Appl. No.: 14/932,732

(22) Filed: Nov. 4, 2015

(65) Prior Publication Data
US 2017/0123103 A1    May 4, 2017

(51) Int. Cl.
*G01V 9/00*    (2006.01)
*E21B 47/10*    (2012.01)
(Continued)

(52) U.S. Cl.
CPC .......... *G01V 9/005* (2013.01); *E21B 47/1005* (2013.01); *G01F 1/74* (2013.01);
(Continued)

(58) Field of Classification Search
CPC ..................................................... G01V 9/005
See application file for complete search history.

(56) References Cited

U.S. PATENT DOCUMENTS 5,892,176 A    4/1999   Pruett
6,920,395 B2   7/2005   Brown
(Continued)

FOREIGN PATENT DOCUMENTS

EP   0508894 A1   10/1992
EP   2184438 A2    5/2010
(Continued)

OTHER PUBLICATIONS

WO ISR and Written opinion dated Feb. 13, 2017 issued in connection with corresponding Application No. PCT/US2016/060425.
(Continued)

*Primary Examiner* — Clayton E Laballe
*Assistant Examiner* — Dennis Hancock
(74) *Attorney, Agent, or Firm* — GE Global Patent Operation; Pabitra K. Chakrabarti

(57) ABSTRACT

A fluid sensor cable assembly and method uses one or more conductive bodies extending along an elongated core body for conducting a heating current to heat the cable assembly. The one or more conductive bodies also are configured to conduct an interrogation signal and to conduct reflections of the interrogation signal. One or more optical fibers extend along the length of the core body and include temperature sensitive elements at different locations along the length of the core body. The temperature sensitive elements measure heat flux out of the cable assembly at the different locations subsequent to heating the cable assembly and communicate the heat flux to a computer acquisition system.

20 Claims, 12 Drawing Sheets

(51) Int. Cl.

| | | |
|---|---|---|
| *G01N 27/02* | (2006.01) | |
| *G01F 1/74* | (2006.01) | |
| *G01N 9/04* | (2006.01) | |
| E21B 47/06 | (2012.01) | |
| G01F 1/688 | (2006.01) | |
| G01N 25/00 | (2006.01) | |

(52) U.S. Cl.
CPC ............... *G01N 9/04* (2013.01); *G01N 27/02* (2013.01); *E21B 47/06* (2013.01); *G01F 1/6884* (2013.01); *G01N 25/00* (2013.01)

(56) References Cited

U.S. PATENT DOCUMENTS

| | | |
|---|---|---|
| 6,933,491 B2 | 8/2005 | Maida, Jr. |
| 6,943,340 B2 | 9/2005 | Tubel et al. |
| 7,045,767 B2 | 5/2006 | Peng et al. |
| 7,880,133 B2 | 2/2011 | Johansen |
| 2007/0040557 A1 | 2/2007 | Johnstad et al. |
| 2007/0158064 A1* | 7/2007 | Pribnow ............. E21B 47/1005 166/250.01 |
| 2008/0264631 A1 | 10/2008 | Mendez et al. |
| 2012/0186570 A1 | 7/2012 | Bosselmann et al. |
| 2013/0227837 A1 | 9/2013 | Varkey et al. |
| 2013/0261977 A1 | 10/2013 | Shanks |
| 2014/0260588 A1 | 9/2014 | Jaaskelainen et al. |
| 2014/0290335 A1* | 10/2014 | Shanks ............... E21B 47/1005 73/25.05 |
| 2014/0294041 A1* | 10/2014 | Zhang .................... G01F 1/684 374/54 |
| 2016/0266277 A1* | 9/2016 | Blackburn ............. G01L 9/007 |

FOREIGN PATENT DOCUMENTS

| | | |
|---|---|---|
| EP | 2635770 B1 | 10/2014 |
| WO | 2013045913 A2 | 4/2013 |
| WO | 2013076479 A1 | 5/2013 |

OTHER PUBLICATIONS

Shang Ying et al., Research of Optical Fiber Fluid Flow Monitoring System Based on Flow-Induced Pipe Vibration; 2012 Symposium on Photonics and Optoelectronics (SOPO); May 21-23, 2012; pp. 1-3.

Kawase M et al., Simple-structure optical fiber cables manufactured without stranding processes,; Journal of Lightwave Technology; Aug. 1988; vol. 6, Issue: 8, pp. 1280-1284.

Fibercore Fibercore Fiberpeadia Coating; <http://fibercore.com/expertise/fiberpaedia/coating>; pp. 1-2, accessed Oct. 19, 2015.

Microwave Photonics Research Laboratory; <http://www.site.uottawa.ca/~jpyao/mprg/Equipment.html>; pp. 1-5, accessed Oct. 19, 2015.

Heyvaert, Stefaan et al., Optical Fiber Manufacturing: Stack-and-draw technique creates ultrasmall-diameter endoscopes—Laser Focus World, Dec. 13, 2013; <http://www.laserfocusworld.com/articles/print/volume49/issue12/features/opticalfibermanufacturingstackand-drawtechniquecreatesultrasmalldiamete>; accessed Oct. 19, 2015.

* cited by examiner

FLUID SENSOR CABLE ASSEMBLY, SYSTEM, AND METHOD

FIELD

Embodiments of the subject matter disclosed herein relate to assemblies, systems, and methods for measuring fluid velocities and/or measuring fluid phases.

BACKGROUND

Multiphase measurement devices can be placed into wells to measure the individual phase flow rates of different phases flowing in the wells. These devices can only be placed into non-producing wells, or during time periods that a well is not producing resources (e.g., during times when oil or other resources are not being extracted from the well). The devices can measure the flow rates of fluids flowing in the wells. These measurements can be used to improve the production of resources (e.g., oil) from the wells, limit wear and tear (e.g., corrosion) on components in the well (by tracking the amount of water and gas in the well), represent performance of the wells, etc.

Some of these devices measure the flow rates by heating the well with elongated cables extending down into the wells and monitoring the cooling of the well. But, it can require a significant amount of time to heat the well, and the well may not heat evenly. The long heating time and uneven heating can limit the resolution and accuracy of the measurements obtained by the devices. Additionally, these devices are limited to measuring the flow rates during times when resources are not being extracted from the well. As a result, these devices cannot provide real time measurements of flow rates, or the rates of flow of fluids in the well during the same time period that one or more of the fluids are being extracted from the well.

Additionally, these devices may be able to measure the total rate of each of several different fluid constituents in the well. For example, the devices may be unable to measure the different amounts of oil, water, and/or gas in the well. Instead, the devices may be limited to measuring the total rate of flow of these fluids, but not individual flow rates or amounts of the different fluids.

BRIEF DESCRIPTION

In one embodiment, a fluid sensor cable assembly includes an internal core body, one or more conductive bodies, and one or more optical fibers. The internal core body has a length that is elongated from a first end to an opposite second end. The one or more conductive bodies extend along the length of the core body, and are configured to conduct a heating current along the length of the core body to heat the fluid sensor cable assembly. The one or more conductive bodies also are configured to conduct an interrogation signal along the length of the core body and to conduct reflections of the interrogation signal as distributed phase measurement signals to a computer acquisition system. The one or more optical fibers extend along the length of the core body at a designated radial distance from a center axis of the core body. The one or more optical fibers include a plurality of temperature sensitive elements disposed at different locations along the length of the core body. The temperature sensitive elements are configured to measure heat flux out of the fluid sensor cable assembly at the different locations along the length of the core body subsequent to heating the fluid sensor cable assembly by the one or more conductive bodies and communicate the heat flux that is measured via the one or more optical cables to the computer acquisition system.

In one embodiment, a method (e.g., for measuring distributed phases and/or flow velocities in a subterranean well) includes conducting a distributed phase interrogation signal along one or more conductive bodies extending along an elongated core body of a fluid sensor cable assembly and receiving distributed phase measurement signals along the one or more conductive bodies in response to conducting the interrogation signal. The distributed phase measurement signals are reflected back along the conductive coil at different locations along a length of the fluid sensor cable assembly and represent an amount of one or more phases of fluid flowing outside of the fluid sensor cable assembly. The method also includes heating the fluid sensor cable assembly by conducting a heating current for a designated period of time along one or more of the conductive bodies and, subsequent to heating the fluid sensor cable assembly, receiving temperature measurements from temperature sensitive elements in one or more optical fibers of the fluid sensor cable assembly at different locations along the length of the fluid sensor cable assembly. The temperature measurements represent heat flux out of the fluid sensor cable assembly at the different locations.

In one embodiment, a fluid sensor system includes one or more fluid cable assemblies and a computer acquisition system. The one or more fluid sensor cable assemblies are configured to be disposed in one or more subterranean wells. The one or more fluid cable assemblies include an elongated internal core body and one or more optical cables extending along a length of the one or more fluid sensor cable assemblies and having temperature sensitive elements. The one or more cable assemblies also include one or more conductive coils wrapped around the core body along the length of the one or more fluid sensor cable assemblies. The computer acquisition system is configured to be operatively coupled with the one or more fluid sensor cable assemblies. The computer acquisition system is configured to conduct, for at least one of the fluid sensor cable assemblies, a distributed phase interrogation signal along the one or more conductive coils and is configured to receive distributed phase measurement signals conducted along the one or more conductive coils in response to conducting the interrogation signal. The distributed phase measurement signals are reflected back along the one or more conductive coils at different locations along the length of the fluid sensor cable assembly and represent amounts of different phases of the fluid at the different locations. The computer acquisition system also is configured to heat the at least one fluid sensor cable assembly by conducting a heating current along at least one of the conductive coils and, subsequent to heating the at least one fluid sensor cable assembly, to receive temperature measurements from the temperature sensitive elements at the different locations along the length of the at least one fluid sensor cable assembly, the temperature measurements representative of heat flux out of the fluid sensor cable assembly.

BRIEF DESCRIPTION OF THE DRAWINGS

Reference is made to the accompanying drawings in which particular embodiments and further benefits of the invention are illustrated as described in more detail in the description below, in which.

DETAILED DESCRIPTION

One or more embodiments of the inventive subject matter described herein provide cable assemblies, measurement systems, and methods that measure distributed phases (e.g., water cut, gas content, etc.) and flow velocity in an oil well. The system and method can provide for real-time logging across multiple perforations, multiple zones and horizontals, as well as enable reservoir production optimization and real time drainage management. The measurements provided by the systems and methods can help validate seismic models of oil fields, improve reservoir planning, increase reserves, improve fracture management, and increase production rates. The systems and methods can log producing formation, as well as net production and be useful in managing the use of water, gas, and sand in wells.

The systems and methods can use a distributed anemometer with fiber optic distributed temperature sensitive elements coupled to one or more heating element. Radio frequency (RF) signals can be used to measure the different phases of the fluids at different locations along the length of the cable assemblies disposed inside the wells.

Figure 1:
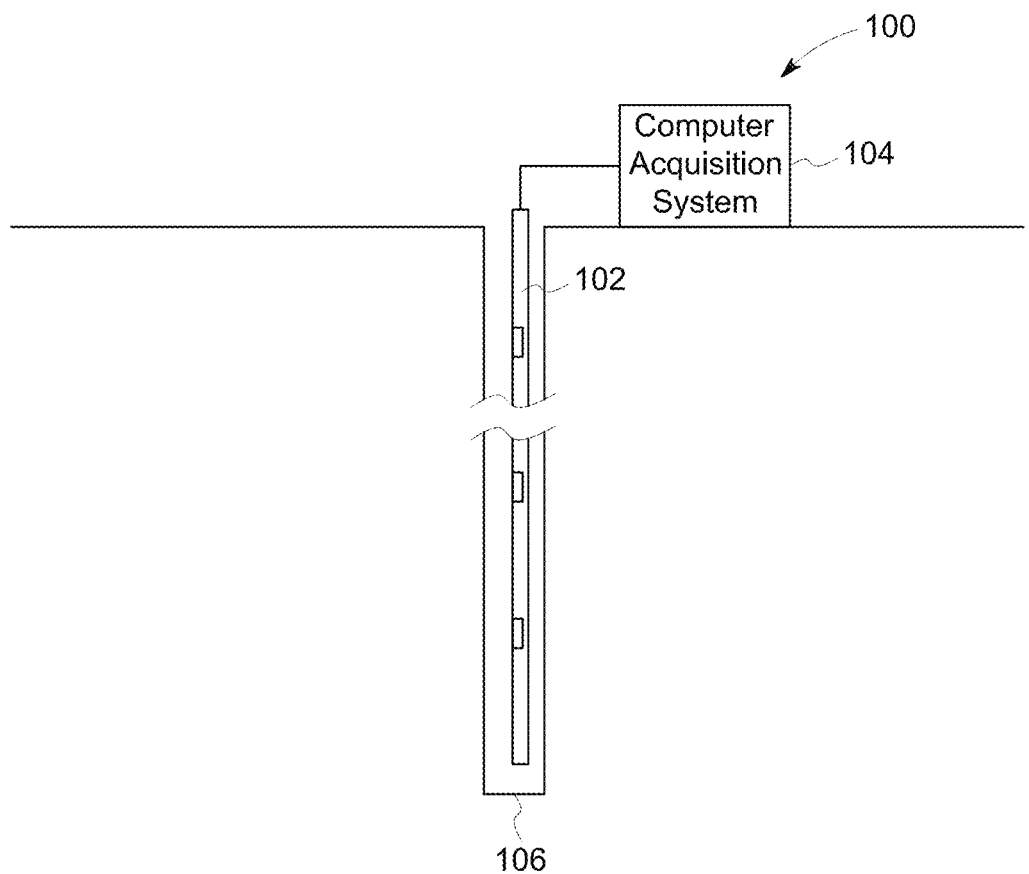
FIG. 1 illustrates one embodiment of a fluid measurement system.

FIG. 1 illustrates one embodiment of a fluid measurement system 100. The system 100 may be used to measure fluid flow velocities and distributed phase measurements within a subterranean well 106, such as an oil well. For example, the system 100 may measure the rates at which oil, water, and/or gas flow within the well, as well as how much oil, water, and/or gas there is within the well. The system 100 can be a distributed measurement system in that the system 100 concurrently measures the flow velocities of fluids along the exterior surface of the cable assembly 102 and the distributed phase measurements at multiple different locations within the well.

The system 100 includes one or more fluid sensor cable assemblies 102 and a computer acquisition system 104. The cable assembly 102 may be elongated between opposite ends 106, 108, which may be several hundred or thousand feet apart from each other. The cable assemblies 102 include sensing devices that measure characteristics of the fluids in a well that represent the flow velocities and distributed phase measurements. Some of the sensing devices are shown in FIG. 1 as temperature sensitive elements 110. As described below, the cable assembly 102 may include additional sensors. Several cable assemblies 102 may be disposed in different wells in a field and communicatively coupled with the same computer acquisition system 104. The computer acquisition system 104 represents one or more computer devices, such as hardware circuitry that includes and/or is connected with one or more processors (e.g., microprocessors, field programmable gate arrays, integrated circuits, or other electronic logic-based devices). The computer acquisition system 104 receives the characteristics measured by the sensing devices of the cable assembly 102 and determines the flow velocities and distributed phase measurements based on the measured characteristics. The system 100 can measure the flow velocities and/or phase measurements in real time. For example, the cable assembly 102 can be inserted into the well 106 to measure the flow velocities and/or phase measurements at the same time that one or more resources (e.g., oil and/or gas) are being removed from the well 106. In one embodiment, the cable assembly 102 is able to measure both flow velocities and distributed phases within the well 106. Alternatively, the cable assembly 102 may only measure flow velocities or distributed phases, but not both, within the well 106. For example, the cable assembly 102 may have fewer components than described below and may measure the flow velocities but not the distributed phases within the well 106. This can help make the form factor (e.g., size) of the cable assembly 102 smaller than a cable assembly 102 that measures both distributed phases and flow velocities.

Figure 2:
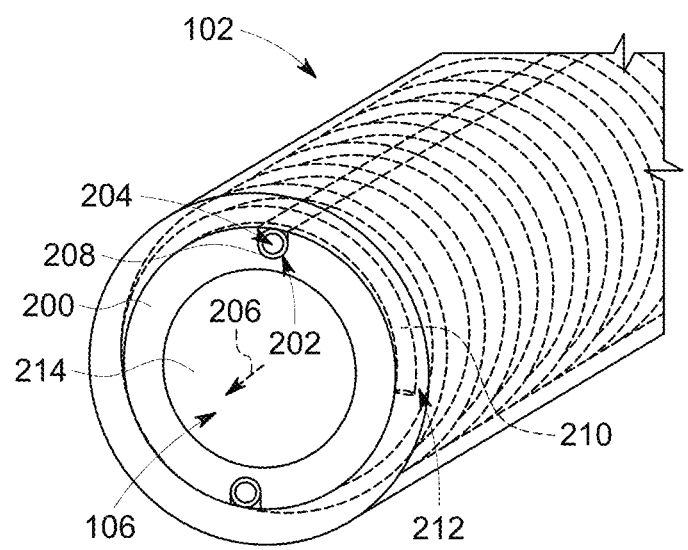
FIG. 2 illustrates one end of the cable assembly shown in FIG. 1 according to one embodiment.

FIG. 2 illustrates one end 106 of the cable assembly 102 shown in FIG. 1 according to one embodiment. The cable assembly 102 includes an internal core body 214 that supports additional components of the cable assembly 102. The core body 214 may be formed from a rope, such as a polypropylene extruded rope, nylon, another polyamide, Kevlar®, or another material. Alternatively, the core body 214 may be another type of elongated body other than a rope. A coating 200 is disposed around the core body 214 in the illustrated embodiment. The coating 200 may be formed from a similar material as the core body 214, such as polypropylene. In one embodiment, the coating 200 is extruded onto the core body 214. Alternatively, the coating 200 may be provided around the core body 214 in another manner.

One or more slots 202 are formed into the cable assembly 102 as shown in FIG. 2. These slots 202 may be cut into the exterior of the coating 200 to designated radial depths of the cable assembly 102. The slots 202 may extend the same radial distance from a center axis 206 of the cable assembly 102. The slots 202 may linearly extend along the exterior of the coating 200. Optical fibers 204 are disposed within the slots 202. In the illustrated embodiment, the optical fibers 204 and slots 202 are on opposite sides of the cable assembly 102 (e.g., the fibers 204 and slots 202 are located at the twelve and six o'clock positions on a clock), but alternatively, the fibers 204 and slots 202 may be located in other positions (e.g., may not be opposite each other). While two fibers 204 and two slots 202 are shown in FIG. 2, the cable assembly 102 optionally may include more than two fibers 204 and/or more than two slots 202, or may include a single fiber 204 and a single slot 202. Alternatively, the slots 202 and fibers 204 may helically wrap around the cable assembly 102 to allow for the optical fibers 204 to move with the cable assembly 102 as the cable assembly 102 changes length (e.g., elongate during heating).

The fibers 204 may be disposed inside dielectric tubes 208 in the slots 202, such as plastic tubes. In some embodiments the fiber may be disposed inside metal tubes 208 in the slots 202. The fibers 204 may have a carbon coating and/or the tubes 208 may hold a gel material, such as a hydrogen scavenging gel. The fibers 204 may be embedded within such a gel inside the tubes 208. Optionally, the fibers 204 may be coated with carbon or a metal such as copper-nickel alloy, aluminum or gold.

The optical fibers 204 may be disposed in the slots 202 to prevent buckling of the fibers 204 during spooling and unspooling of the cable assembly 102. If the optical fibers 204 are not placed into the slots 202 (for example, if the optical fibers 204 extend along the exterior of the coating 200, the optical fibers 204 may experience increased strain during bending of the cable assembly 102 and/or form kinks. The cable assembly 102 may be wound around a reel or other device during manufacture and for storage, transportation, etc. During winding or unwinding of the cable assembly 102, the optical fibers 204 may experience increased strain and may bend or otherwise become damaged if the optical fibers 204 are not located in the slots 202. The optical fibers 204 may be placed into the slots 202 with extra slack such that placing the optical fibers 204 in the slots 202, however, reduces the strain experienced by the fibers 204 and, as a result, the fibers 204 do not buckle during winding or unwinding of the cable assembly 102. The slot also helps relieve strain that may be experience downhole in an oil well due to deviations in the well.

The temperature sensitive elements 110 shown in FIG. 1 can represent fiber Bragg gratings (FBGs) in the optical fibers 204. The temperature sensitive elements 110 may use distributed Raman temperature sensing to provide multiple temperature measurements at different locations along the length of the cable assembly 102. For example, the temperature sensitive elements 110 may reflect one or more wavelengths of light along the fibers 204 back to the computer acquisition system 104 shown in FIG. 1. The wavelength of light that is reflected by a temperature sensitive element 110 may change based on the temperature at and/or around the temperature sensitive element 110. The temperature sensitive elements 110 may be spaced apart from each other along the length of the cable assembly 102 to provide distributed temperature measurements. As described herein, changes in the temperatures sensed by the temperature sensitive elements 110 may be used to calculate flow velocities at or near the different temperature sensitive elements 110. Providing multiple temperature sensitive elements 110 at different locations along the cable assembly 102 allow for the flow velocities to be measured at different depths in a well.

One or more conductive bodies 210 may extend along the length of the cable assembly 102. The conductive bodies 210 can include one or more wires that are helically wound around the exterior of the coating 200. Alternatively, one or more of the conductive bodies 210 may be linear and linearly extend along the length of the cable assembly 102. In the illustrated embodiment, the conductive bodies 210 extend over the temperature sensitive elements 110. For example, the conductive bodies 210 may be radially outside of the temperature sensitive elements 110 and optical fibers 204. Alternatively, the conductive bodies 210 may be beneath the temperature sensitive elements 110 and optical fibers 204 such that the temperature sensitive elements 110 and optical fibers 204 are radially outside of the conductive bodies 210. In some embodiments the conductive bodies 210 run in parallel with the optical fibers 204 within the slots.

At least one of the conductive bodies 210 may be a heating element that heats the cable assembly 102. The heating element can conduct a heating current to heat the cable assembly 102. The computer acquisition system 104 may include and/or be connected with a power source that supplies the current. As described below, the computer acquisition system 104 may conduct the current through the heating element for a designated time period that partially heats the cable assembly 102. For example, instead of heating the cable assembly 102 for a sufficiently long time to heat all of the cable assembly 102 (e.g., the entire thickness) to the same temperature, the computer acquisition system 104 may cause the heating element to heat the cable assembly 102 for a shorter time period. As a result, the cable assembly 102 may not be heated to the same temperature through the entire thickness of the cable assembly 102.

The computer acquisition system 104 can control conduction of a heating current supplied from a power supply, such as a utility grid, one or more batteries, generators, alternators, capacitors, etc. In one embodiment, the computer acquisition system 104 controls conduction of current from a capacitor that stores electric energy during time periods that the cable assembly 102 is not being heating, but that conducts the energy as the heating current during time periods that the cable assembly 102 is heated. Using such a capacitor can allow for the power supply to be a lower rated power supply than would be used if a utility grid is used to supply the heating current.

The computer acquisition system 104 can control the amount of thermal energy transferred to the cable assembly 102 from the heating element by controlling various parameters of the heating current that is conducted through the heating element. These parameters can include the duration that the heating current is conducted through the heating element, the magnitude of the heating current (e.g., the amount of amperes or volts conducted through the heating element), how often the heating current is conducted (e.g., the frequency at which the heating current is pulsed), and/or the number of duty cycles used to conduct the heating current through the heating element.

The same conductive body 210 that is the heating element also can be used to conduct an electric signal (e.g., a radio frequency or RF signal) along the length of the cable assembly 102 to determine amounts of different phases of fluid in the well and to heat the cable assembly 102. Alternatively, two different conductive coils may be used for conducting the signal and heating the cable assembly 102. The conductive bodies 210 can include a marker coil that is separated into segments along the length of the cable assembly 102. Alternatively, the marker coil may not be a coil but may have another shape, such as a linear wire. The marker coil may be a coil that is segmented such that the coil includes gaps at different locations along the length of the cable assembly 102. These gaps interrupt a conductive pathway along the marker coil. The gaps may be provided as designated locations along the length of the cable assembly 102, such as every ten feet or other distance. As described below, the gaps help to identify locations along the length of the cable assembly 102 where phase measurements are made based on reflections of a signal conducted along at least one of the conductive bodies 210. The reflections can be used to determine the amounts of different phases (e.g., oil, gas, and/or water) at the locations of the different gaps. For example, depending on characteristics of waveforms in the reflected signal, the computer acquisition system 104 can determine the relative amounts of the different phases at the different depths in the well.

In one embodiment, the temperature sensitive elements 110 may be heating elements that heat the cable assembly 102 instead of or in addition to the conductive body 210 described above. For example, the temperature sensitive elements 110 may be metallized and conductively coupled with one or more of the conductive bodies 210. Current conducted from the computer acquisition system 104 to the metallized temperature sensitive elements 110 can cause the temperature sensitive elements 110 to heat the cable assembly 102, similar to as described herein in connection with the conductive bodies 210. In one embodiment, the heating element in the cable assembly 102 includes regions of lower electrical resistances connected with regions of larger electrical resistances. For example, the heating element can include a conductive wire having a first diameter in first portions of the length of the wire and periodic smaller diameters having larger resistances. The larger resistance portions of the wire form localized heating elements. Conduction of current by the wire can result in the larger resistance portions heating localized areas of the cable assembly 102. Optionally, resistors may be conductively coupled with at least one of the conductive bodies 210. These resistors may be located at, on, or beneath the temperature sensitive elements 110, and can locally heat the cable assembly 102 when a heating current is conducted through the conductive body 210 or bodies 210 that are connected with the resistors.

A protective layer 212 is disposed outside of the conductive bodies 210, the coating 200, the tubes 208, and the optical fibers 204 in the illustrated embodiment. The protective layer 212 may be formed from a tape that is wound around the conductive bodies 210, the coating 200, the tubes 208, and the optical fibers 204. As one example, the protective layer 212 may be formed from polytetrafluoroethylene tape, such as Teflon™. Additionally or alternatively, the protective layer 212 may be formed in another manner or with another material. For example, the protective layer 212 may be extruded around the tape, the conductive bodies 210, the coating 200, the tubes 208, and the optical fibers 204. The protective layer 212 may be resistant to chemicals such as oil, corrosive gases, water, etc. The operating temperature range of the protective layer may be above 200 degrees Celsius. One example of a material that can be used to form the protective layer 212 includes perfluoroalkoxy alkane (PFA 350 available from DuPont™).

In one embodiment, the coating 200 and/or the protective layer 212 may be formed from one or more materials to control the thermal conductivity of the cable assembly 102. For example, to increase the thermal conductivity of the cable assembly 102, one or more conductive particles (e.g., particles formed from boron nitride, aluminum oxide, or other high thermal conductivity materials) may be embedded within the coating 200 and/or protective layer 212.

Figure 3:
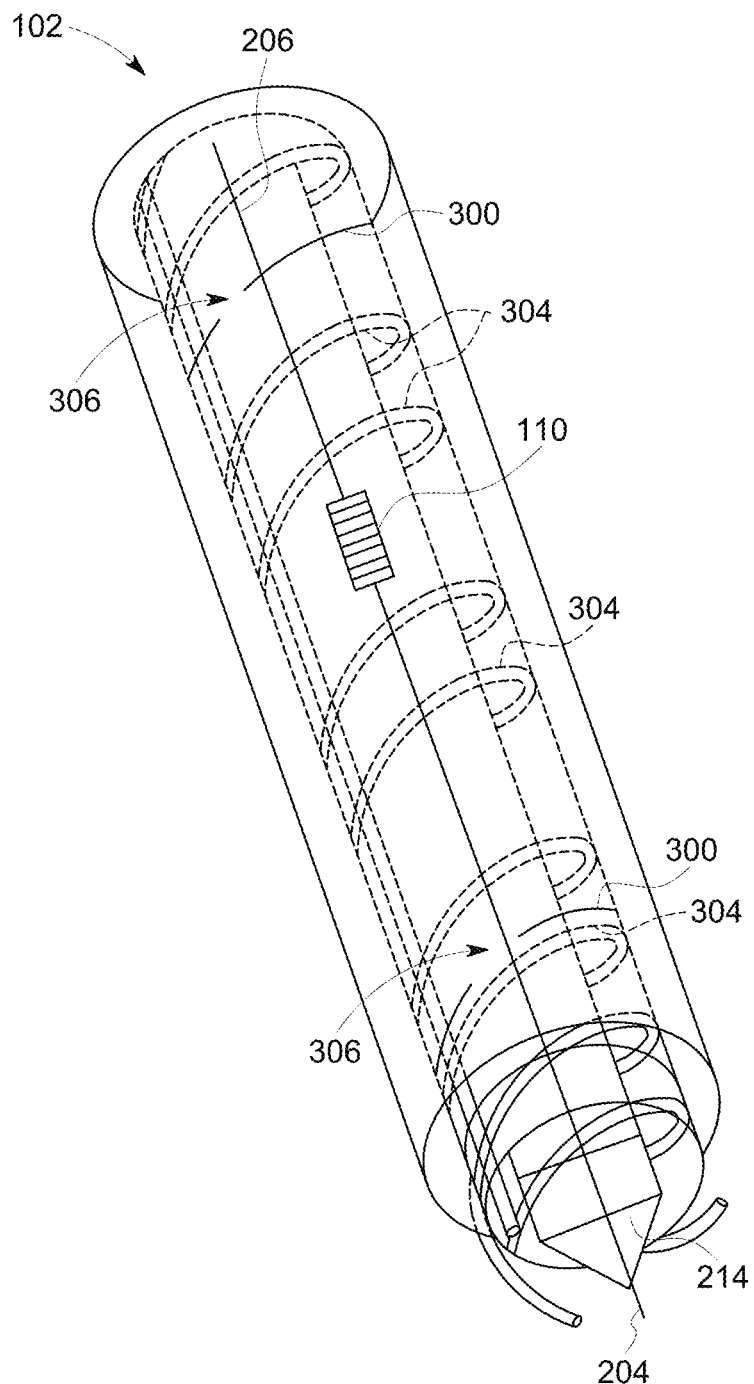
FIG. 3 illustrates a perspective view of one segment of the cable assembly shown in FIGS. 1 and 2 according to one embodiment.

FIG. 3 illustrates a perspective view of one segment of the cable assembly 102 shown in FIGS. 1 and 2 according to one embodiment. Several of the conductive bodies 210 are shown in FIG. 3, including the marker coil 300 and a heating element 304. The number and/or arrangement of the conductive bodies 210 may differ from the illustrated embodiment. As shown, the marker coil 300 and the heating element 304 helically wrap around the core body 214 of the cable assembly 102, which is schematically illustrated in FIG. 3. The marker coil 300 includes gaps 306 that reflect signals conducted along the signaling coil 302, as described above. These gaps 306 assist in identifying where waveforms of reflected signals indicate different phases within the well, as described below. The signaling coil 302 may continuously extend along the length of the cable assembly 102 and may not include the gaps 306.

The heating element 304 helically wraps around the core body 214. In one aspect, one or more of the heating elements 304 may be located beneath one or more temperature sensitive elements 110. Additionally or alternatively, one or more of the heating elements 304 may be located above one or more of the temperature sensitive elements 110.

Figure 4:
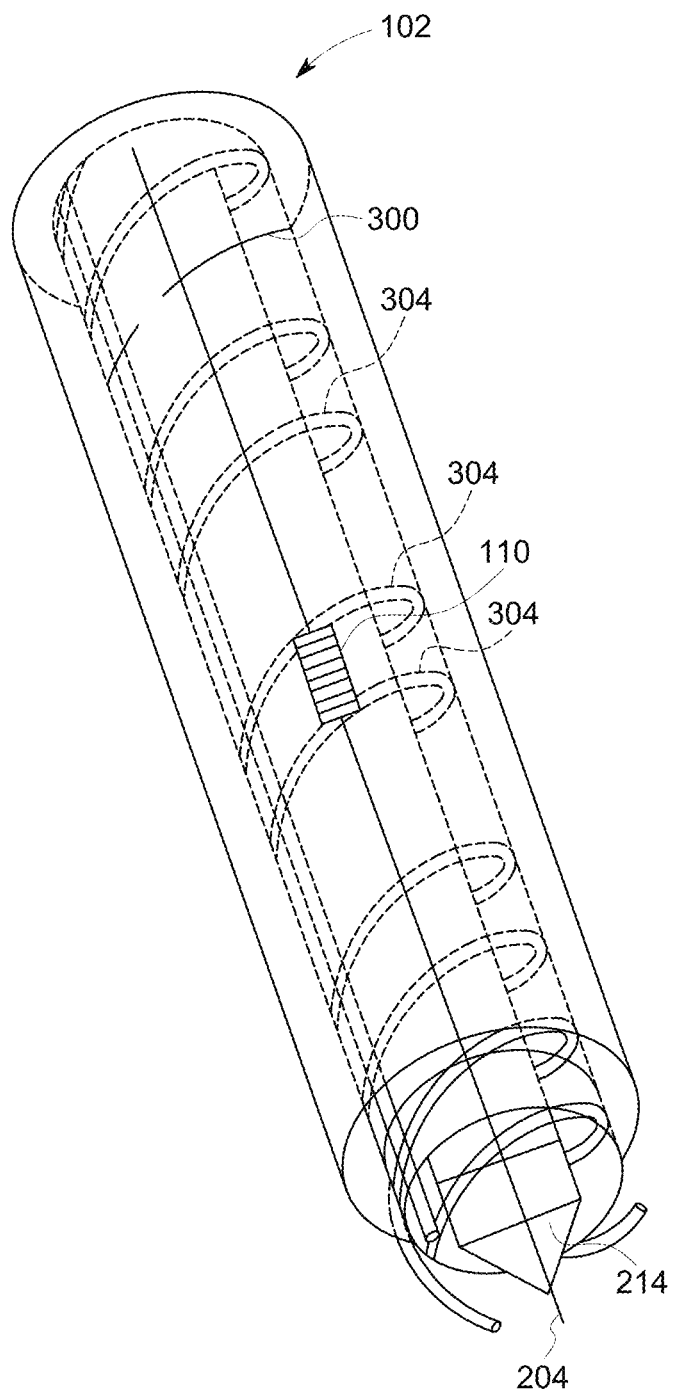
FIG. 4 illustrates a perspective view of another segment of the cable assembly shown in FIGS. 1 through 3 according to one embodiment.

FIG. 4 illustrates a perspective view of another segment of the cable assembly 102 shown in FIGS. 1 through 3 according to one embodiment. The portion of the heating element 304 shown in FIG. 4 helically wraps around the core body 214, and also extends above or beneath one or more of the temperature sensitive elements 110 of the optical fibers 204. The heating element 304 may be located on top of the temperature sensitive element 110. Optionally, the heating element 304 may be located beneath the temperature sensitive element 110.

Each temperature sensitive element 110 may be located between consecutive wraps of the heating element 304 around the cable assembly 102, or may be located above or beneath the heating element 304. In FIG. 3, the temperature sensitive element 110 is located between neighboring wraps of the heating element 304 around the cable assembly 102. In FIG. 4, the temperature sensitive element 110 is located above or beneath one of the wraps of the heating element 304 around the cable assembly 102.

The data provided by the temperature sensitive elements 110 may need to be calibrated depending on which temperature sensitive elements 110 are outside of or inside the heating element 304 (e.g., as shown in FIG. 4), and which temperature sensitive elements 110 are not outside of or inside the heating element 304 (e.g., as shown in FIG. 3). For example, the heating element 304 may heat the cable assembly 102 when the cable assembly 102 is submerged in a medium of a known response to the heat. The measured changes in temperature from the temperature sensitive elements 110 may be examined and compared to designated changes in temperature that should occur by the heat generated by the heating element 304. Differences between the measured changes in temperature and the designated changes in temperature at the various temperature sensitive elements 110 can be used to calibrate the measured changes in temperature when the cable assembly 102 is submerged in a well. As another example, the computer acquisition system 104 may synchronize data obtained from the cable assembly 102 with data acquired from one or more other sensors in the well. For example, an electrically submersible pump (ESP) may be disposed on the well to pump one or more fluids in the well. The ESP may be controlled by the computer acquisition system 104 (or the computer acquisition system 104 may communicate with the system that controls the ESP) such that the computer acquisition system 104 knows the rate at which the ESP is pumping fluid at one or more locations in the well. The computer acquisition system 104 can track the temperature changes measured using the cable assembly 102 and match these changes with the known fluid flow velocity from the ESP to calibrate the cable assembly 102 to the well. As another example, one or more temperature and/or pressure sensors may be disposed at the bottom of the well and may be communicatively coupled with the computer acquisition system 104. These sensors may measure the temperatures and/or pressures at the bottom of the well and communicate this data to the computer acquisition system 104. The computer acquisition system 104 may measure temperatures using the cable assembly 102 and match these temperatures with the temperatures measured by the other sensors to calibrate the cable assembly 102.

Figure 5:
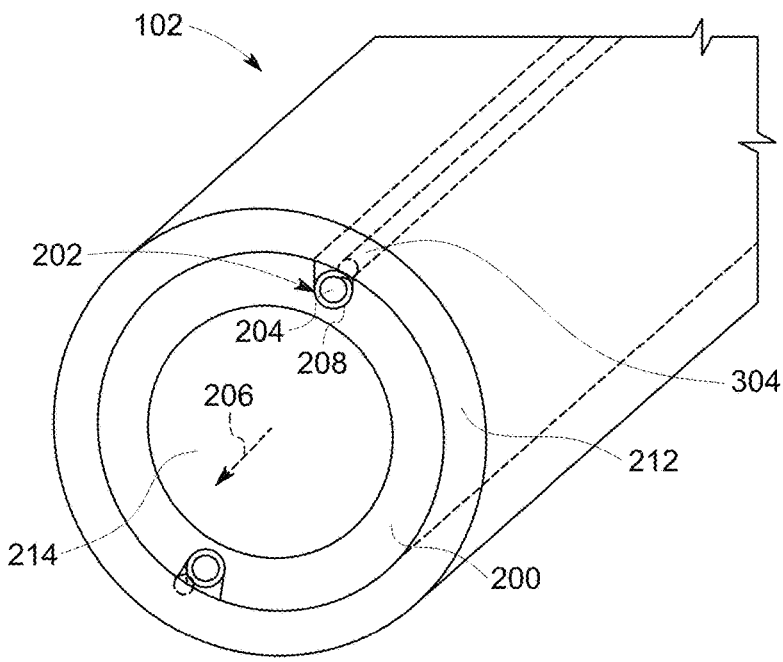
FIG. 5 illustrates the cable assembly shown in FIG. 1 according to another embodiment.

FIG. 5 illustrates the cable assembly 102 shown in FIG. 1 according to another embodiment. In contrast to the cable assembly 102 shown in FIGS. 2 through 4, the heating element 304 of the cable assembly 102 shown in FIG. 5 may be an elongated, linear heating element or wire, instead of a helical coil as shown in FIGS. 2 through 4. The heating element 304 shown in FIG. 5 may be heating in a similar manner as described above to allow the system 100 (shown in FIG. 1) to measure flow velocities, as described herein.

In operation, one or more embodiments of the cable assembly 102 described herein is placed into a subterranean well to measure flow velocities and amounts of different phases of fluids flowing in the well and outside of the cable assembly 102. For example, the cable assembly 102 may concurrently measure the amounts of oil, gas, and water, as well as the velocity at which the oil, gas, and/or water is flowing, at multiple different locations along the length of the cable assembly 102. Subsequent to inserting the cable assembly 102 into a well, an electric signal is conducted from the computer acquisition system 104 along one or more of the conductive bodies 210, such as the heating element 304 or another coil. This signal may be a radio frequency (RF) signal or other type of signal. This signal is conducted along a conductive body 210 and is reflected back up the conductive body 210 to the computer acquisition system 104 at locations of or near the gaps 306 in the marker coil 300. The reflections of the signal can be used to determine the amounts of different phases at the different locations of reflection. The reflected signals may be referred to as distributed phase measurement signals.

Figure 6:
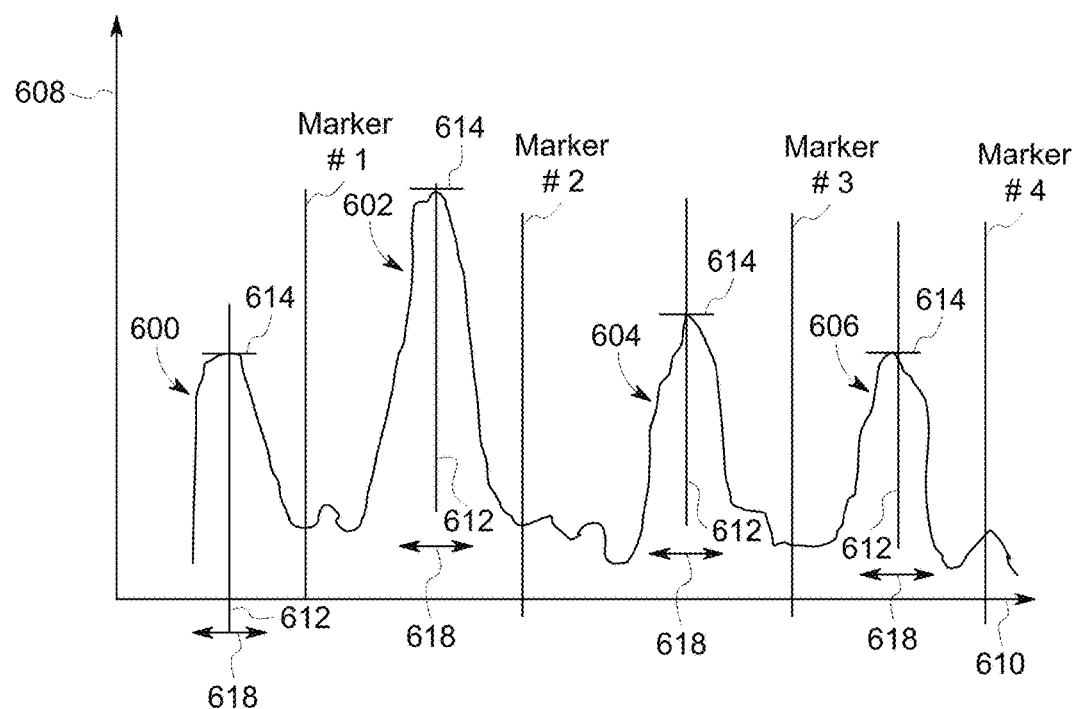
FIG. 6 illustrates waveforms of an electric signal that is reflected back along at least one conductive body of the cable assembly (shown in FIG. 2) according to one example.

FIG. 6 illustrates waveforms 600, 602, 604, 606 of the electric signal reflected back along the conductive body 210 according to one example. The waveforms 600, 602, 604, 606 can represent the signal that is measured by the computer acquisition system 104 via the conductive body 210 in response to conducting an RF signal or other signal along the conductive body 210. The signal is a reflected signal and is shown alongside a horizontal axis 610 representative of time or distance along the cable assembly 102 and a vertical axis 608 representative of magnitudes of the reflected signal.

The computer acquisition system 104 may generate the signal (e.g., an RF signal, which may be referred to herein as an interrogation signal or a distributed phase interrogation signal) for conduction along at least one of the conductive bodies 210 for a designated period of time, and then stop generating the interrogation signal. The signal is conducted in the conductive body 210 along the length of the cable assembly 102, and is reflected back along the conductive body 210 to the computer acquisition system 104. The reflections may occur at various locations along the length of the cable assembly 102. The marker coil 300 may be capacitively coupled with the conductive body 210 through which the interrogation signal is conducted. The reflections of the interrogation signal may indicate where the gaps 306 in the marker coil 300 are located. For example, the reflections of the interrogation signal may include decreases or gaps that indicate where the gaps 306 in the marker coil 300 are located.

The reflections of the interrogation signal are measured by the computer acquisition system 104 and may include waveforms, such as the waveforms 600, 602, 604, 606. The waveforms 600, 602, 604, 606 may be associated with different locations along the length of the cable assembly 102 away from the computer acquisition system 104 based on the time delay between transmitting the interrogation signal and receiving the reflections of the signal. For example, the waveform 600 may be associated with locations closer to the computer acquisition system 102 than the waveforms 602, 604, 606 because the time of flight between generating the interrogation signal and receiving the waveform 600 is less than the time of flight for the waveforms 602, 604, 606. The locations of the gaps 306 in the marking coil 300 along the length of the cable assembly 102 may be known from previous measurements, and the locations associated with the waveforms 600, 602, 604, 606 along the length of the cable assembly 102 may be determined relative to the gaps 306 based on the time of flights of the different waveforms 600, 602, 604, 606. For example, the speed at which the interrogation signal is conducted and reflected along the conductive body 210 may be known and used to calculate the locations along the cable assembly 102 that are associated with the waveforms 600, 602, 604, 606. In the illustrated embodiment, the locations of several gaps 306 in the marker coil 300 (referred to as "Marker #1", "Marker #2", etc., in FIG. 6) are shown in FIG. 6. The gaps 306 may be referred to as markers, and may be located every twenty-five feet or other distance along the length of the cable assembly 102.

In one embodiment, the waveforms 600, 602, 604, 606 are indicative of wave velocities in the fluid flowing outside of the cable assembly 102. One or more characteristics of the waveforms 600, 602, 604, 606 can be examined to determine the amounts of different phases of the fluid at the different locations along the cable assembly 102. In one aspect, the characteristics of the waveforms 600, 602, 604, 606 located between neighboring markers in the reflected signal may be determined and used to calculate amounts of different phases in the well at the locations between the markers. These characteristics may include, for example, locations or times 612 at which the peak amplitudes 614 of the waveforms occur. The locations or times 616 at which the peak amplitudes 614 occur can represent when the peak amplitudes 614 are measured along the horizontal axis 610 and/or where along the cable assembly 102 that the peak amplitudes 614 occur.

Several interrogation signals may be generated by the computer acquisition system 104, several reflections of the signals may be measured by the computer acquisition system 104, characteristics of the waveforms 600, 602, 604, 606 in the reflected signals may be determined by the computer acquisition system 104, and the computer acquisition system 104 may determine changes in the characteristics. For example, the computer acquisition system 104 may measure or calculate velocities 618 (e.g., rates of change of the locations or times 616) of the waveforms 600, 602, 604, 606 by determining how rapidly the locations or times 616 of the peak amplitudes 604 change between the same markers from different reflected signals. These velocities can indicate the amounts of different phases of the fluid that are present between the different markers. For example, a first designated rate of change in the location or time 616 of the waveform 600 can indicate that a first ratio of 20% water, 10% gas, and 70% oil is outside of the cable assembly 102 between the first and second markers, while a different, second designated rate of change in the location or time 616 for the waveform 602 can indicate that a different, second ratio of water, gas, and oil is outside of the cable assembly 102 between the first and second markers (e.g., 40% water, 20% gas, and 40% oil). Other changes in the characteristics of the waveforms may indicate other amounts of the different phases of the fluids outside of the cable assembly 102.

The computer acquisition system 104 may heat the cable assembly 102 using the heating coil 304 shown in FIGS. 3 and 4. The computer acquisition system 104 can conduct an electric heating current through the heating coil 304 to at least partially heat the cable assembly 102. In one embodiment, the computer acquisition system 104 may only partially heat the cable assembly 102 by alternating between conducting the heating current through the heating coil 304 during a first designated time period, stopping conduction of the heating current for a subsequent, second designated time period, and repeating the conducting and stopping conduction of the heating current during one or more heating iterations. The time periods in which the heating current is conducted through the heating element 304 to heat the cable assembly 102 may be sufficiently short to avoid heating the entire cable assembly 102 to a designated temperature. For example, the heating time period in which the heating current is being conducted may be of a short enough duration to increase the temperature of the cable assembly 102 in an outer thickness dimension of the cable assembly 102, but not of a long enough duration to increase the temperature of the entire core body 214 (shown in FIG. 2) of the cable assembly 102 to the same temperature as the exterior of the cable assembly 102. Alternatively, the computer acquisition system 104 may conduct the heating current through the heating coil 304 for a sufficiently long time to heat the entire cable assembly 102 to at least the same temperature.

Figure 7:
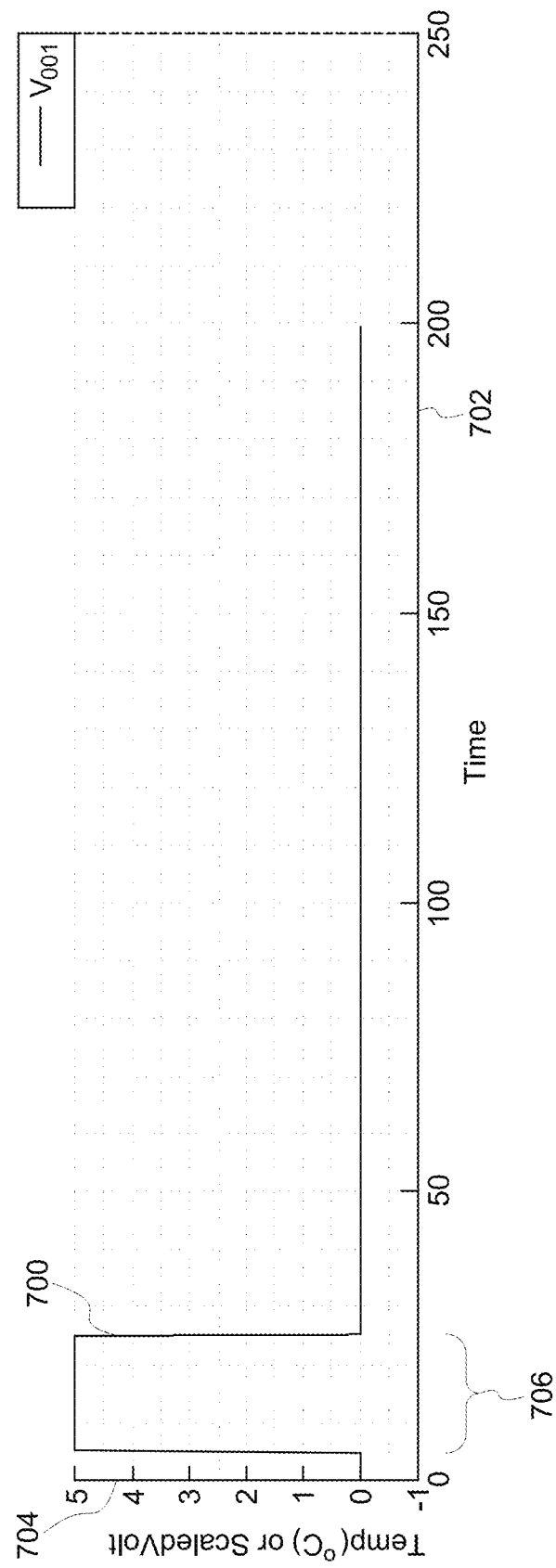
FIG. 7 illustrates a heating current that a computer acquisition system shown in FIG. 1 conducts through a heating element shown in FIG. 3 during a heating cycle according to one embodiment.

FIG. 7 illustrates a heating current 700 that the computer acquisition system 104 conducts through the heating element 304 during a heating cycle according to one embodiment. The heating current 700 represents a voltage conducted in the heating element 304, and is shown along a horizontal axis 702 representative of time and a vertical axis 704 representative of magnitudes of the voltage. The heating current 700 is conducted along the heating element 304 for a designated time period 706 that is not long enough to heat the entirety of the cable assembly 102 to a common temperature. The heating cycle shown in FIG. 7 may be repeated one or more additional times in order to measure the flow velocities along the exterior surface of the cable assembly 102.

In one embodiment, the magnitude and/or duration of the heating cycle can be modified based on a measured flow velocity. The amount of voltage (e.g., magnitude) of the heating current 700 and/or the time period 706 (e.g., duration) at which the heating current 700 is conducted through the heating element 304 can change based on a previously measured flow velocity. For example, for faster flow velocities, the magnitude and/or duration of the heating current 700 can be increased relative to slower flow velocities. The larger magnitude and/or longer duration may be used to heat the cable assembly 102 to a hotter temperature. The increased temperature may cause a subsequent measurement of the flow velocity to be more accurate, as more heat flux can exit the cable assembly 102 into the faster moving fluids outside of the cable assembly 102.

Subsequent to at least partially heating the cable assembly 102, the computer acquisition system 104 may receive temperature measurements from the temperature sensitive elements 110 via the optical fibers 204. The temperature measurements represent changes in the temperature of the cable assembly 102 as measured by the temperature sensitive elements 110 at different locations along the length of the cable assembly 102. The temperature sensitive elements 110 may be fiber Bragg grating reflectors that reflect one or more designated wavelengths of light, but allow other wavelengths to pass through the reflectors. The computer acquisition system 104 may generate light that propagates through the optical fibers 204 to the temperature sensitive elements 110. Different temperature sensitive elements 110 can reflect different wavelengths of light back through the optical fibers 204 to the computer acquisition system 104. Changes in the temperature of the cable assembly 102 can change the wavelengths of light that are reflected by the different temperature sensitive elements 110. As a result, the computer acquisition system 104 can monitor changes in the wavelengths of the light reflected by the different temperature sensitive elements 110 to track cooling of the cable assembly 102 (e.g., after heating the cable assembly 102). The shift or change in the wavelengths of light reflected by different temperature sensitive elements 110 can represent heat flux out of the cable assembly 102. This heat flux can be indicative of flow velocities of the fluid outside of the cable assembly 102 at different locations along the length of the cable assembly 102. Alternatively, the temperature sensitive elements 110 can represent other sensors that are capable of measuring the heat flux out of the cable assembly 102, such as thermocouples.

Figure 8:
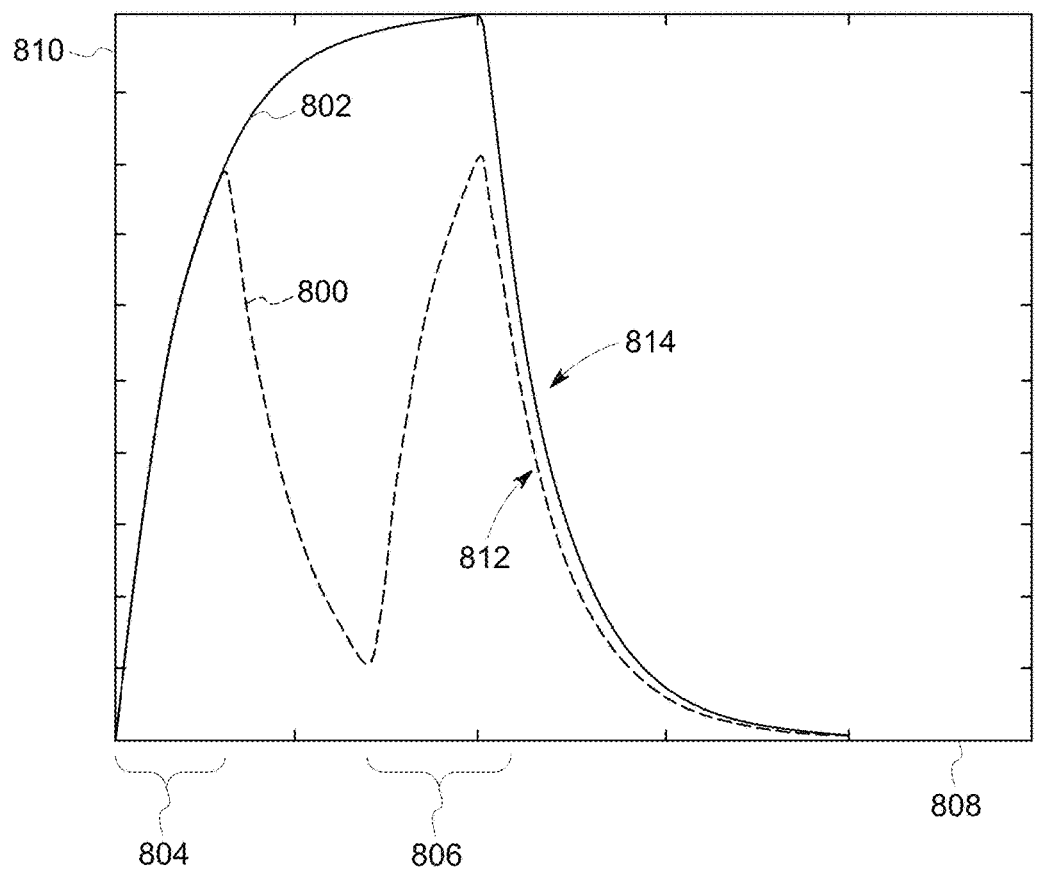
FIG. 8 illustrates temperatures of the cable assembly according to one example.

FIG. 8 illustrates temperatures 800, 802 of the cable assembly 102 according to one example. The temperatures 800 represent temperatures that the cable assembly 102 is heated to by conducting the heating current 700 (shown in FIG. 7) during two heating cycles occurring during different time periods 804, 806. The temperatures 802 represent temperatures of the cable assembly 102 that is heated to when the cable assembly 102 is heated for a longer time period (e.g., to heat the entire cable assembly 102 to the same temperature). The temperatures 800, 802 are shown alongside a horizontal axis 808 representative of time and a vertical axis 810 representative of temperature.

The temperatures 800, 802 initially increase at the same rate. Because the heating cycle ends in one embodiment at the end of the first time period 804, the temperatures 800 to which the cable assembly 102 is actually heated to begin decreasing, but increase again during the subsequent second time period 806. Rates of cooling 812, 814 of the temperatures 800, 802 represent how quickly the cable assembly 102 cools after heating, or the amount of heat flux out of the cable assembly 102. As shown in FIG. 8, the rate of cooling 812 the cable assembly 102 after partially heating the cable assembly 102 is the same as the rate of cooling 814 the cable assembly 102 were heated for a longer period of time. Because the rate of cooling can be used to determine the flow velocities along the exterior surface of the cable assembly 102 (as described below), the system 100 can only partially heat the cable assembly 102 in order to measure the flow velocities, thereby saving time and energy. The cable assembly 102 may be heated to a lower average temperature (relative to heating the cable assembly 102 for longer periods of time), while still providing the same rate of cooling used for determining flow velocities.

Figure 9:
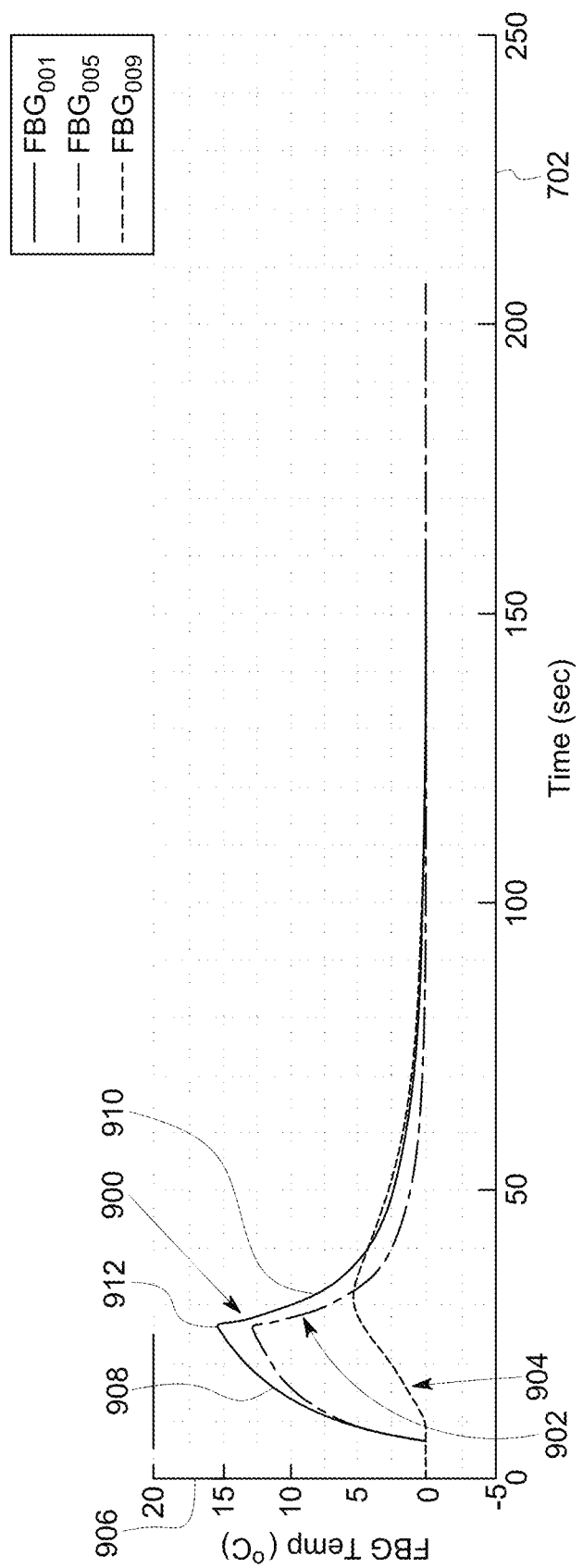
FIG. 9 illustrates temperatures measured by temperature sensitive elements of the cable assembly according to one example.

FIG. 9 illustrates temperatures 900, 902, 904 measured by three temperature sensitive elements 110 of the cable assembly 102 according to one example. The temperatures 900, 902, 904 are shown alongside the horizontal axis 702 representative of time and a vertical axis 906 representative of magnitudes of the temperatures. Each of the temperatures 900, 902, 904 is represented as a waveform having a rising edge 908 and a falling edge 910 separated from each other by a peak 912. In one aspect, the temperatures 900, 902, 904 may represent the temperatures and heat flux out of the cable assembly 102 from the heating cycle shown in FIG. 7.

The computer acquisition system 104 may examine the waveforms of the temperatures 900, 902, 904 following different heating cycles 706 to determine one or more characteristics of the waveforms. The computer acquisition system 104 may then calculate or estimate velocities at which fluids flow along the exterior surface of the cable assembly 102 at the respective locations of the temperature sensitive elements 110. In one embodiment, the computer acquisition system 104 may determine differences in the peaks 912 of the temperatures measured by the same heat sensitive element 110. For example, the computer acquisition system 104 may determine whether a peak temperature 912 measured by the same temperature sensitive element 110 increases or decreases (and/or how much the peak temperature 912 increases or decreases) in consecutive heating cycles 700. This analysis may be repeated for the temperatures measured by other temperature sensitive elements 110. The differences between the peaks 712 in different heating cycles 700 can represent the heat flux out of the cable assembly 102 following heating of the cable assembly 102. Faster velocities of fluid outside of the cable assembly 102 can cause the peaks 712 in the temperatures to decrease by larger amounts relative to slower fluid velocities. For example, if the peaks decrease in value by a first amount (or the peaks increase) at a first temperature sensitive element 110 but the peaks decrease in value by a larger, second amount (or the peaks do not increase) at a different, second temperature sensitive element, then the computer acquisition system 104 may determine that the flow velocity of the fluid outside of the cable assembly 102 is faster at the second temperature sensitive element 110 than the first temperature sensitive element 110. The computer acquisition system 104 may be calibrated to equate different changes in the peaks of the temperatures with different flow velocities. Upon determining a change in the peak temperatures, the computer acquisition system 104 can determine the flow velocity associated with the change.

Optionally, the computer acquisition system 104 may determine one or more decrease characteristics of the temperatures 900, 902, 904 to determine the flow velocities. A decrease characteristic can be a measurement or feature of the temperatures 900, 902, 904 indicative of the decrease in temperatures following a peak temperature 912. For example, a rate at which the temperatures 900, 902, 904 decrease after the respective peak temperature 912 may be a decrease characteristic determined by the computer acquisition system 104. As another example, a time period over which the temperatures 900, 902, 904 decrease from the peak temperature 912 to a lower designated temperature (e.g., the axis 702; a percentage of the peak temperature 912, such as 10%, 15%, or the like; or another value) may be a decrease characteristic determined by the computer acquisition system 104.

Figure 10:
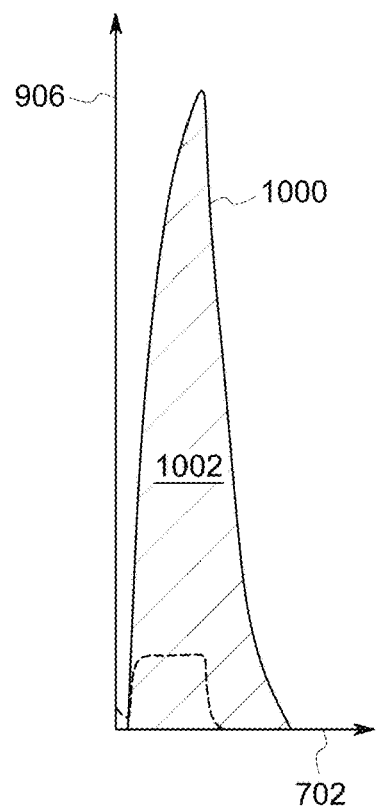
FIG. 10 illustrates temperatures measured by a temperature sensitive element of the cable assembly according to another example.

FIG. 10 illustrates temperatures 1000 measured by a temperature sensitive element 110 of the cable assembly 102 according to another example. The temperatures 1000 are shown alongside the horizontal axis 702 and the vertical axis 906 described above. The temperatures 1000 are measured by the computer acquisition system 104 based on the output from a temperature sensitive element 110 of the cable assembly 102 subsequent to different heating time periods, similar to the temperatures 900, 902, 904 shown in FIG. 9.

The computer acquisition system 104 may examine the temperatures 1000 (or waveforms of the temperatures 1000) to determine one or more characteristics of the temperatures 1000. The computer acquisition system 104 may then calculate or estimate velocities at which fluids flow by the cable assembly 102 at the location of the temperature sensitive element 110 that measured the temperatures 1000. The flow velocities that are determined may be the rates at which a fluid formed of a mixture of several different phases (e.g., two or more of oil, gas, and/or water) flows at different locations in the well, or may be the rates at which different phases of the fluid flows at one or more locations (e.g., the flow velocity of oil, the flow velocity of gas, and/or the flow velocity of water). In one example, an integral 1002 of the temperatures 1000 may be a decrease characteristic determined by the computer acquisition system 104. The integral 1002 can be measured as the area bounded by the temperatures 1000 and the horizontal axis 702, an area bounded by the temperatures 1000 and another boundary, such as a designated percentage of the peak temperature of the temperatures 1000 (e.g., 1%, 5%, 10%, or the like).

The decrease characteristic or characteristics described herein can represent the heat flux out of the cable assembly 102 following heating of the cable assembly 102. Faster velocities of fluid outside of the cable assembly 102 can cause the characteristics to change more rapidly than slower velocities. For example, the rate at which the temperatures decrease following heating may be larger (e.g., the falling edge or side of the temperatures 910 may be more vertical or the slope of the temperatures after the peak 912 may have a larger negative value) for faster flow velocities and smaller (e.g., the falling edge or side 910 of the temperatures may be less vertical or the slope after the peak 912 may have a smaller negative value) for slower flow velocities.

As another example, the time period over which the temperatures decrease may be shorter for faster flow velocities and longer for slower flow velocities. This time period can be referred to as a cooling time period and can begin at the peak 912 of the temperatures and end when the temperatures decrease by a designated amount, such as 100%, 90%, 80%, or the like, of the peak temperature 912. The time period may be shorter for faster flow velocities because the faster moving fluids can carry heat away from the cable assembly 102 faster than slower flow velocities and, as a result, cool the cable assembly 102 over a shorter time period.

As another example, the integral of the temperatures may decrease for faster flow velocities and decrease by smaller amounts (or increase) for slower flow velocities. The integral may be smaller for faster flow velocities because the faster moving fluids can carry heat away from the cable assembly 102 faster than slower flow velocities and, as a result, cool the cable assembly 102 over a shorter time period. Consequently, the size of the integral may become smaller as the temperatures do not increase as much and/or decrease at faster rates relative to slower flow velocities.

The computer acquisition system 104 optionally may examine noise (e.g., an amount of fluctuation, such as a standard deviation) in the temperatures sensed using the temperature sensitive elements 110 to determine flow velocities at different locations along the length of the cable assembly 102 and/or to identify where a fluid is flowing into the well in which the cable assembly 102 is located.

Figure 11:
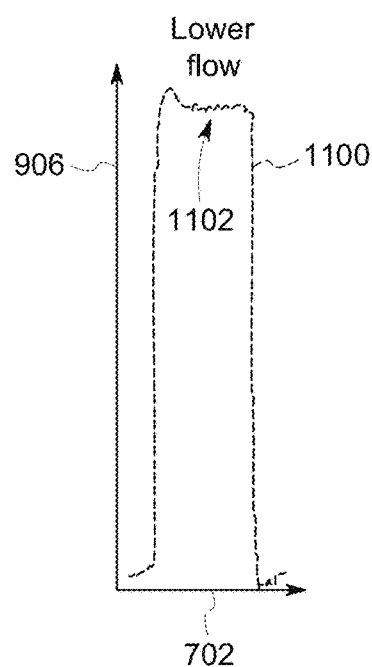
FIG. 11 illustrates temperatures measured by a temperature sensitive element of the cable assembly according to another example.
Figure 12:
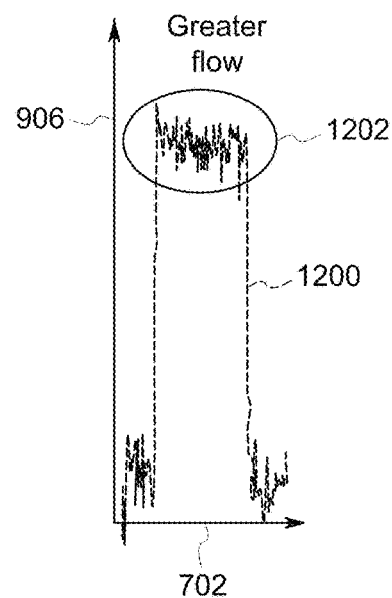
FIG. 12 illustrates additional temperatures measured by the same or different temperature sensitive element of the cable assembly according to one example.

FIG. 11 illustrates temperatures 1100 measured by a temperature sensitive element 110 of the cable assembly 102 according to another example. FIG. 12 illustrates additional temperatures 1200 measured by the same or different temperature sensitive element 110 of the cable assembly 102 according to one example. The temperatures 1100, 1200 are shown alongside the horizontal axis 702 and the vertical axis 906 described above.

The temperatures 1100, 1200 include different amounts of noise 1102, 1202. The noise 1102, 1202 can represent fluctuations in the measured temperature 1100, 1200 that are not caused by corresponding fluctuations in the actual temperature of the cable assembly 102. For example, the noise 1102, 1202 can be random changes in the temperatures 1100, 1200 caused by factors other than the temperature of the cable assembly 102. Vibration can cause the noise 1100, 1200 to be measured by the computer acquisition system 104. The computer acquisition system 104 can examine the temperatures 1100, 1200 measured at different temperature sensitive elements 110 in the cable assembly 102 to determine which temperatures 1100, 1200 exhibit greater noise than other temperatures 1100, 1200. In one embodiment, the noise 1102, 1202 may be measured as standard deviations of the temperatures 1100, 1200 or other quantifiable values representative of variations in the temperatures 1100, 1200.

In the illustrated example, the temperatures 1200 measured by one temperature sensitive element 110 have larger magnitudes of noise 1202 than the temperatures 1100 measured by another temperature sensitive element 110. The noise 1202 in the temperatures 1200 vary by larger amounts than the noise 1102 in the temperatures 1100. The larger magnitudes of the variations in the noise 1202 in the temperatures 1200 relative to the noise 1102 in the temperatures 1100 can indicate that the fluid in the well is flowing at a faster flow velocity at or near the temperature sensitive element 110 that provided the temperatures 1200 than at the temperature sensitive element 110 that provided the temperatures 1100. The faster flow of the fluid can cause the measured temperatures 1200 to fluctuate by larger amounts than the temperatures 1100 measured for slower moving fluid. As a result, the larger noise 1202 can indicate faster flow velocity of the fluid at the temperature sensitive element 110 that measured the temperatures 1200 than at the temperature sensitive element 110 that measured the temperatures 1100.

The flow velocity of the fluid may be determined by the computer acquisition system 104 at several different locations in the cable assembly 102 using the several temperature sensitive elements 110. In one aspect, the computer acquisition system 104 can determine where fluid is being injected into the well based on the temperatures sensed from the temperature sensitive elements 110. For example, the temperatures measured by a first temperature sensitive element 110 that have greater decreases, faster rates of decrease, decreases over shorter time periods, smaller integrals, and/or more noise than the temperatures measured by one or more other temperature sensitive elements 110 may indicate that fluid (e.g., water) is being injected into the well at or near the location of the first temperature sensitive element 110 in the well. These locations can be injection zones, or areas within the well where fluid is inserted into the well from outside of the well.

The flow velocities, the amounts of different phases in the fluid, and/or the injection zones determined by the computer acquisition system 104 from data collected from one or more cable assemblies 102 may be used to characterize one or more wells and/or fields having several wells. This information may be used by the computer acquisition system 104 to generate outputs useful for managing the wells and/or fields.

In one embodiment, one or more additional sensors may be connected with the cable assembly 102 to measure additional or alternate characteristics of the well. For example, a pressure sensor (e.g., a micro-electro-mechanical sensor) may be connected with the distal end of the cable assembly 102 (e.g., the end of the cable assembly 102 that is farthest from the computer acquisition system 104) to obtain measurements of pressure in the well. The sensor may be connected with one or more of the conductive bodies 210 and/or one or more of the optical fibers 204 in order to communicate the measured pressures to the computer acquisition system 104.

Figure 13:
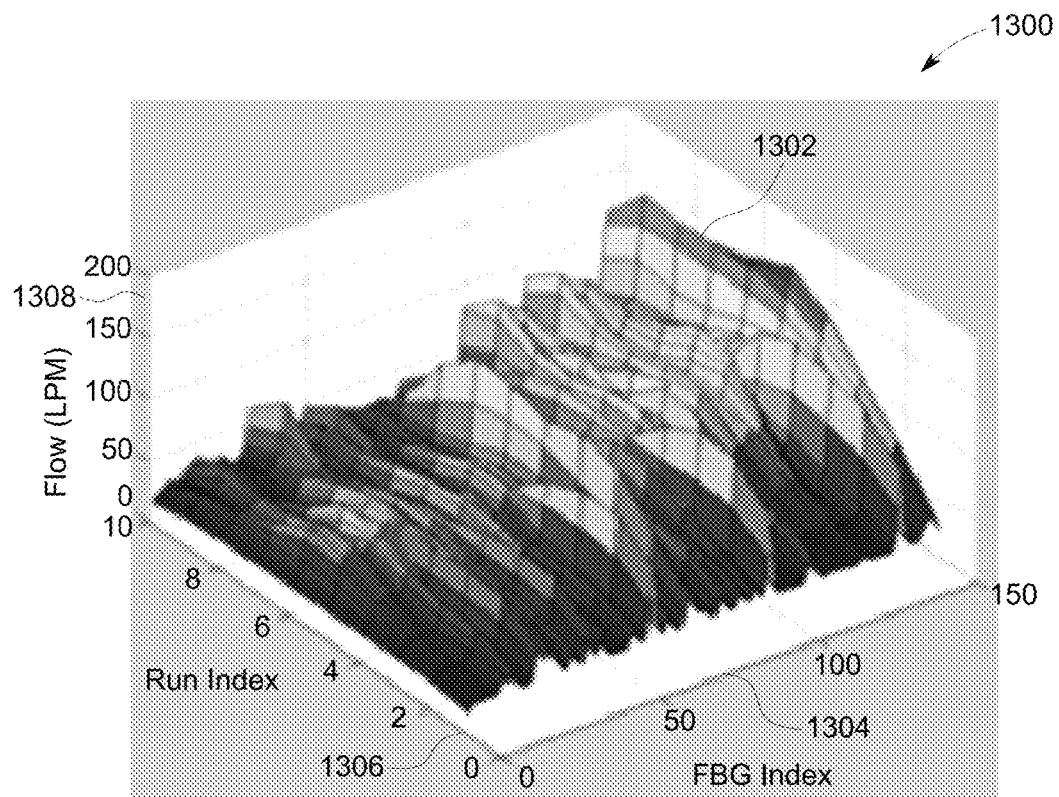
FIG. 13 illustrates an output that may be generated by the computer acquisition system based on the flow velocities measured using several cable assemblies according to one example.
Figure 14:
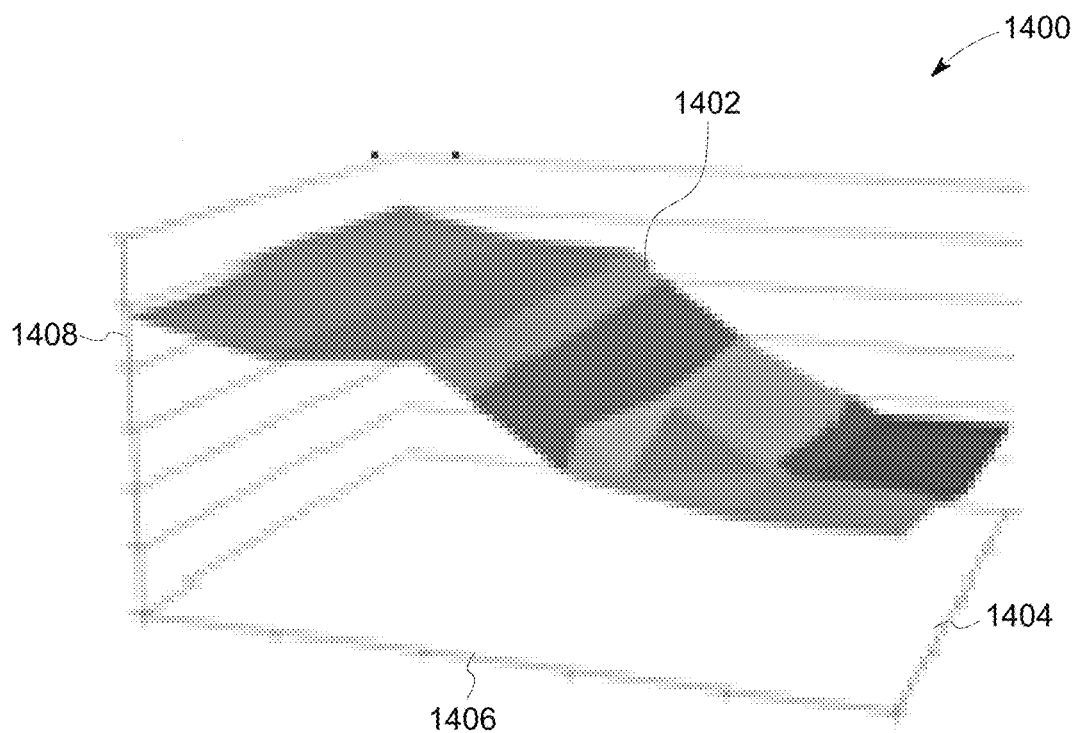
FIG. 14 illustrates an output that may be generated by the computer acquisition system based on the distributed phases measured using several cable assemblies according to one example.

FIGS. 13 and 14 illustrate outputs 1300, 1400 that may be generated by the computer acquisition system 104 based on the flow velocities and/or phases measured using several cable assemblies 102 according to one example. The outputs 1300, 1400 represents a display that may be presented on a display device of the computer acquisition system 104 or another system. The output 1300 visually presents flow velocities 1302 measured at different depths within different wells in a field. The flow velocities 1302 are shown alongside a first orthogonal axis 1304 representative of depths into the wells, a second orthogonal axis 1306 representative of locations of the wells in the field, and a third orthogonal axis 1308 representative of the flow velocities.

The output 1400 visually presents phase amounts 1402 of at least one of the phases (e.g., water or water cut) measured at different depths in different wells. The amounts 1402 may be determined by calculating the distributed phases at different depths in the wells, as described above. The phase amounts 1402 are shown alongside a first orthogonal axis 1404 representative of time, a second orthogonal axis 1406 representative of depths into the wells, and a third orthogonal axis 1408 representative of amounts of one of the phases (e.g., water).

Figure 15:
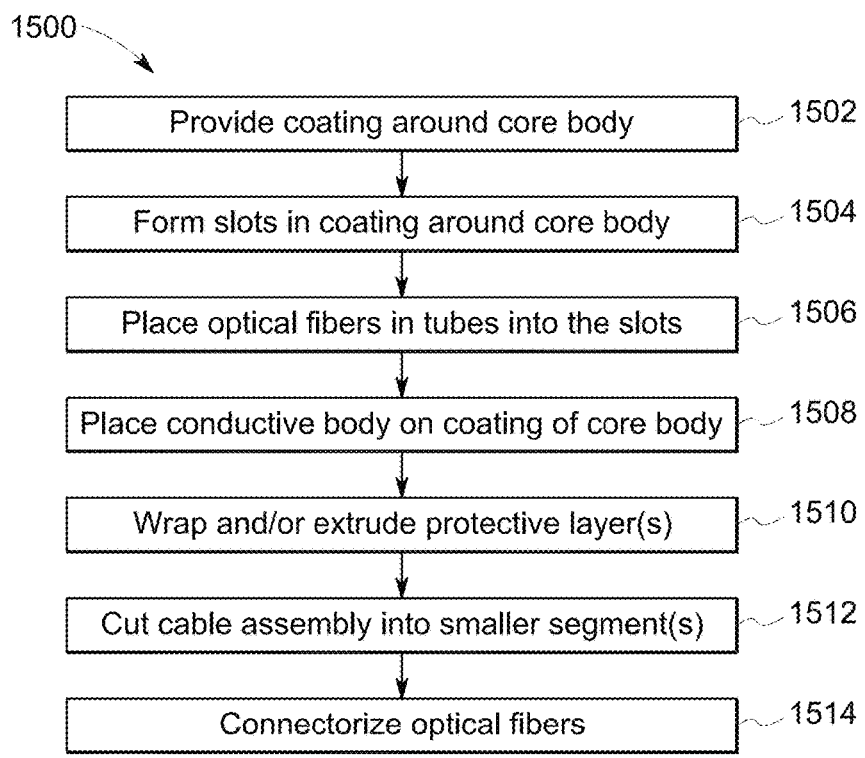
FIG. 15 illustrates a flowchart of one embodiment of a method for manufacturing a fluid sensor cable assembly.
Figure 16:
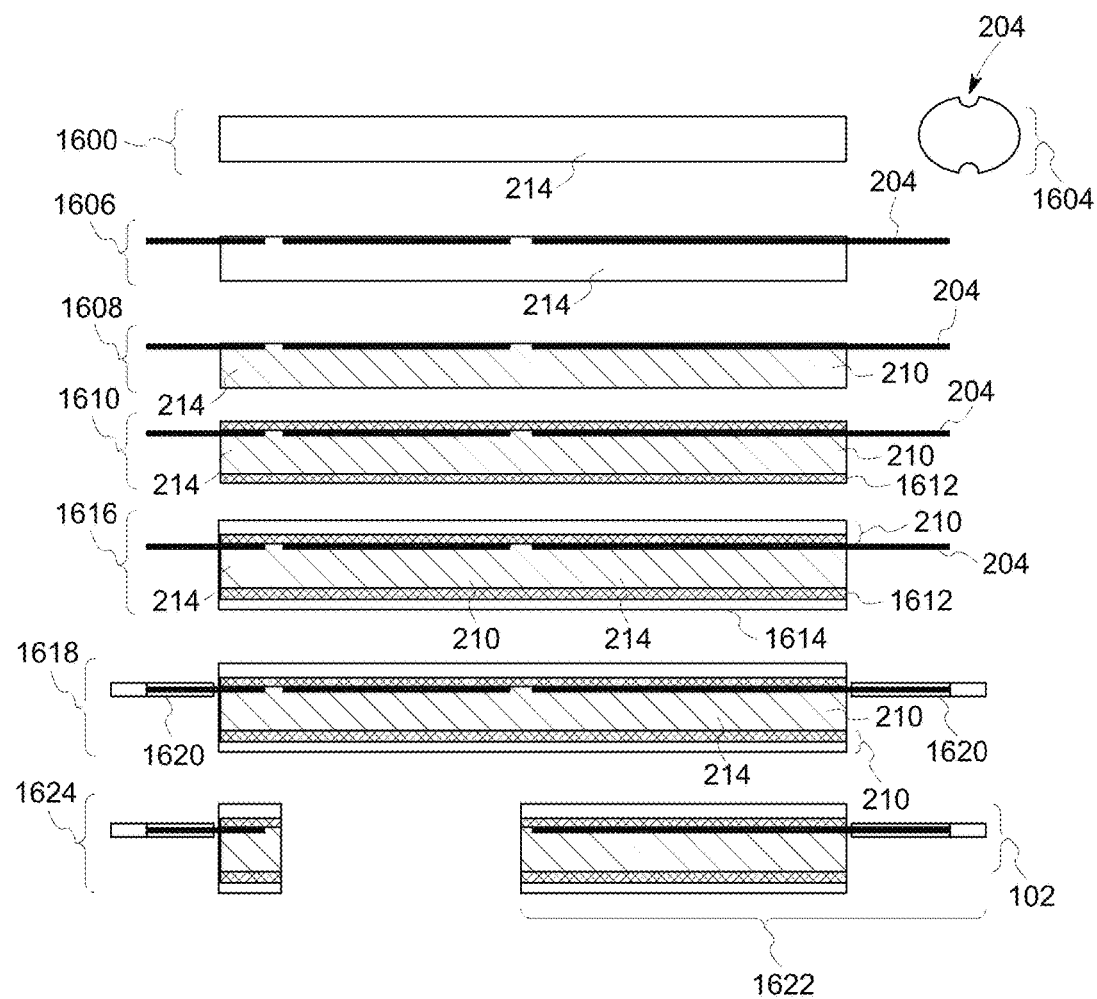
FIG. 16 schematically illustrates different stages of the cable assembly during the manufacturing method represented by the flowchart shown in FIG. 15 according to one example.

FIG. 15 illustrates a flowchart of one embodiment of a method 1500 for manufacturing a fluid sensor cable assembly. FIG. 16 schematically illustrates different stages of the cable assembly during the manufacturing method 1500 represented by the flowchart shown in FIG. 15 according to one example. The method 1500 may be performed to create one or more embodiments of the cable assembly 102 shown in FIGS. 1 through 5. At 1502, a coating is provided around a core body. As shown in FIG. 16, the core body may be a rope or other elongated body 214, as shown in stage 1600. The coating provided on the core body may be formed from a similar material as the core body, such as polypropylene. In one embodiment, the coating is extruded onto the core body. Alternatively, the coating may be provided around the core body in another manner.

At 1504, slots are formed in the coating that is around the core body. The slots can be formed into the coating during extrusion of the coating. For example, the coating may be extruded onto the core body using a die that forms the slots into the coating. Alternatively, the slots can be formed by cutting the slots into the coating. The slots 202 are shown in the exterior of the coating and core body in stage 1604 of FIG. 16.

At 1506, optical fibers inside polymer or metal tubes are placed into the slots, as shown in stage 1606 of FIG. 16. The optical fibers may have a carbon or metal coating and/or the tubes may hold a gel material, such as a hydrogen scavenging gel (such as Sepigel™ H 200LWT from Seppic). The optical fibers may be embedded within such a gel inside the tubes. As described above, the optical fibers may be disposed in the slots to prevent buckling of the fibers. The optical fibers may include temperature sensitive elements, such as fiber Bragg grating reflectors, at different locations along the length of the optical fibers. At 1508, one or more conductive bodies are placed onto the coating that is outside of the core body. As shown in stage 1608 of FIG. 16, the conductive body or bodies 210 may be conductive wire that is helically wrapped around the coating and core body. Optionally, one or more of the conductive bodies may be placed onto the coating along a linear pathway. The conductive body or bodies can include wires or other conductive pathways that are used to conduct current and/or signals for heating the cable assembly, conducting interrogation signals and reflections of the interrogation signals, etc.

In another embodiment, the conductive body or bodies may be beneath the optical fibers. For example, the conductive body or bodies may be wrapped around or placed onto the core body before the coating is placed around the core body, and the optical fibers may be placed into the slots of the coating outside of the conductive body or bodies.

At 1510, one or more protective layers are wrapped and/or extruded onto the conductive body or bodies, the coating, the optical fibers, and the core body. As shown in stage 1610 of FIG. 16, in one embodiment, a protective tape 1612 may be wound around the conductive bodies, the coating, the tubes holding the optical fibers, and the optical fibers. As one example, the protective layer may be formed from polytetrafluoroethylene tape, such as Teflon™. Optionally, the protective layer can include a protective coating 1614 that is extruded around the conductive bodies, the coating, the tubes, and the optical fibers, as shown in stage 1616 of FIG. 16. The protective layer 212 shown in FIG. 2 may be formed from the tape 1612 and the coating 1614 on the tape 1612. One example of a material that can be used to form the coating 1614 includes perfluoroalkoxy alkane (PFA 350 available from DuPont™).

At 1512, the optical fibers are connectorized. As shown in stage 1618 of FIG. 16, electrical connectors 1620 can be coupled with the optical fibers at one end of the cable assembly. The connectors are configured to connect the optical fibers with the computer acquisition system described herein. At 1514, the cable assembly formed by the core body, coating, optical fibers, conductive body or bodies, and protective layer is cut into smaller segments. For example, the cable assembly may be cut into lengths appropriate for insertion into a well by separating the cable assembly into segments 1622, as shown in stage 1624 of FIG. 16.

Figure 17:
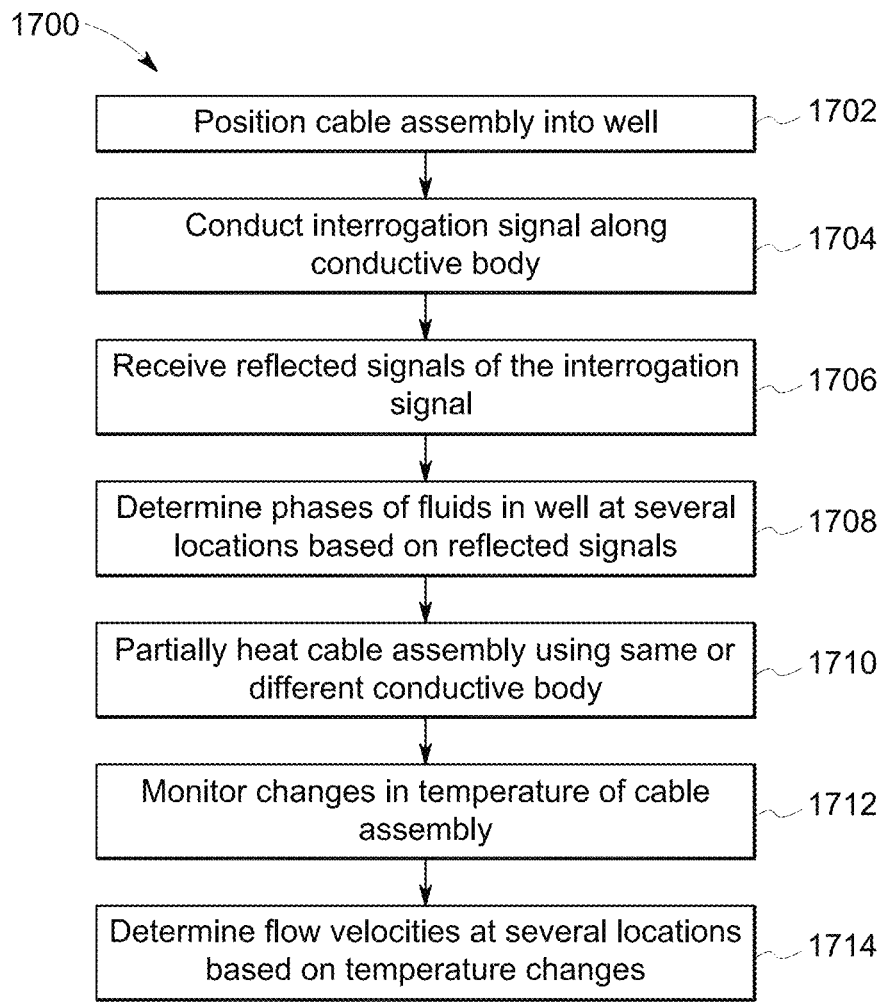
FIG. 17 illustrates a flowchart of one embodiment of a method for measuring distributed phases and flow velocities of fluids in a well.

FIG. 17 illustrates a flowchart of one embodiment of a method 1700 for measuring distributed phases and flow velocities of fluids in a well. The method 1700 may use one or more embodiments of the cable assemblies 102 described herein to measure the content of different phases of fluid (e.g., oil, gas, and/or water) and the flow velocity of the fluid at several different locations in a well. At 1702, the cable assembly is positioned in a well. The cable assembly may be inserted into the well such that the temperature sensitive elements and the markers in the cable assembly are located at different depths or distances in the well.

At 1704, an electric interrogation signal is conducted along one or more of the conductive bodies in the cable assembly. This signal may be an RF signal or other type of signal. The signal is conducted along the conductive body or bodies, and is reflected at different distances or locations in the well. The reflection of the signal is impacted by the amounts of different phases of the fluid flowing outside of the cable assembly at the different distances or locations in the well.

At 1706, the reflected signals of the interrogation signal are conducted along one or more conductive bodies in the cable assembly back to the computer acquisition system. The reflected signals are received and may include waveforms representative of the amounts of different phases in the fluid at different locations along the length of the cable assembly in the well. At 1708, the amounts of the different phases of the fluid in the well at the different locations in the well along the length of the cable assembly are determined based on the reflected signals. One or more different characteristics of the waveforms in the reflected signals may be determined, and changes in these characteristics (e.g., changes in locations or times at which the peaks occur over time) may be calculated in order to determine the different amounts of phases (e.g., oil, gas, and/or water) in the fluid at the different locations, as described above.

At 1710, the cable assembly is at least partially heated using the same or different conductive body as was used to conduct the interrogation signal and/or reflected signals. For example, a current may be conducted along the same conductive coil used to conduct the interrogation signal and the reflections of the interrogation signal in order to partially heat the cable assembly. Alternatively, a different conductive body or coil may be used. The cable assembly may be partially heated, such as by heating the cable assembly for three to four minutes (or another length of time), to avoid heating the entire cable assembly to the same temperature. Alternatively, the entire cable assembly may be heated and/or may be heated for a longer period of time.

At 1712, changes in the temperature of the cable assembly are monitored. After heating the cable assembly, the current used to heat the cable assembly may no longer be conducted in order to stop heating the cable assembly. After a designated period of time following the heating of the cable assembly (e.g., three to four minutes), the temperatures of the cable assembly at different locations may be measured by the temperature sensitive elements in the optical fibers. Changes in these temperatures can be indicative of the heat flux out of the cable assembly.

At 1714, flow velocities of the fluid in the well are determined at several locations along the length of the cable assembly based on the temperature changes. As described above, different characteristics of the temperature changes can be used to determine the rate at which the fluid flows at different locations along the length of the cable assembly.

In one embodiment, a fluid sensor cable assembly includes an internal core body, one or more conductive bodies, and one or more optical fibers. The internal core body has a length that is elongated from a first end to an opposite second end. The one or more conductive bodies extend along the length of the core body, and are configured to conduct a heating current along the length of the core body to heat the fluid sensor cable assembly. The one or more conductive bodies also are configured to conduct an interrogation signal along the length of the core body and to conduct reflections of the interrogation signal as distributed phase measurement signals to a computer acquisition system. The one or more optical fibers extend along the length of the core body at a designated radial distance from a center axis of the core body. The one or more optical fibers include a plurality of temperature sensitive elements disposed at different locations along the length of the core body. The temperature sensitive elements are configured to measure heat flux out of the fluid sensor cable assembly at the different locations along the length of the core body subsequent to heating the fluid sensor cable assembly by the one or more conductive bodies and communicate the heat flux that is measured via the one or more optical cables to the computer acquisition system.

In one aspect, the heat flux may be measured while the assembly is in a subterranean well and one or more resources (e.g., oil and/or gas) are being extracted from the well (as the measurements are being made).

In one aspect, the one or more optical fibers are disposed within a dielectric tube with a hydrogen scavenging gel.

In one aspect, the one or more optical fibers are coated with one or more of carbon or a metal.

In one aspect, the core body includes an exterior coating having slots extending into the exterior coating. The one or more optical fibers are disposed within the slots.

In one aspect, the one or more conductive bodies that conduct the heating current are disposed radially outside of the one or more optical fibers.

In one aspect, the one or more conductive bodies that conduct the heating current are disposed radially inside the one or more optical fibers.

In one aspect, the core body, the one or more optical fibers, and the one or more conductive bodies are configured to be inserted into a subterranean well to measure the heat flux and distributed phases of oil, water, and gases at different depths within the subterranean well.

In one aspect, the temperature sensitive elements include fiber Bragg grating reflectors embedded within the one or more optical fibers.

In one aspect, the temperature sensitive elements measure the heat flux out of the fluid sensor cable assembly using distributed Raman temperature sensing.

In one aspect, the distributed phase measurement signals represent amounts of two or more of water, gas, or oil at one or more different distances along the length of the core body.

In one aspect, the heat flux that is measured at the different locations represents flow velocities of one or more fluids at the different locations along the length of the core body outside of the cable assembly.

In one aspect, the one or more conductive bodies include a single conductive coil helically wound around the core body that conducts the heating current and conducts the distributed phase measurement signals.

In one aspect, the one or more conductive bodies include a first conductive coil helically wound around the core body that conducts the heating current and a separate, second conductive coil helically wound around the core body that conducts the distributed phase measurement signals.

In one aspect, the temperature sensitive elements include metallized portions that are conductively coupled with the one or more conductive bodies. The metallized portions receive the heating current to heat the fluid sensor cable assembly.

In one aspect, the one or more conductive bodies are configured to conduct a radio frequency signal as the interrogation signal.

In one embodiment, a method (e.g., for measuring distributed phases and/or flow velocities in a subterranean well) includes conducting a distributed phase interrogation signal along one or more conductive bodies extending along an elongated core body of a fluid sensor cable assembly and receiving distributed phase measurement signals along the one or more conductive bodies in response to conducting the interrogation signal. The distributed phase measurement signals are reflected back along the conductive coil at different locations along a length of the fluid sensor cable assembly and represent an amount of one or more phases of fluid flowing outside of the fluid sensor cable assembly. The method also includes heating the fluid sensor cable assembly by conducting a heating current for a designated period of time along one or more of the conductive bodies and, subsequent to heating the fluid sensor cable assembly, receiving temperature measurements from temperature sensitive elements in one or more optical fibers of the fluid sensor cable assembly at different locations along the length of the fluid sensor cable assembly. The temperature measurements represent heat flux out of the fluid sensor cable assembly at the different locations.

In one aspect, heating the fluid sensor cable assembly includes alternating between conducting the heating current during a first time period and stopping conduction of the heating current for a subsequent, second time period during one or more heating iterations.

In one aspect, the method also includes determining a flow velocity of one or more fluids outside of the fluid sensor cable assembly based on the temperature measurements.

In one aspect, the flow velocity is determined based on a duration of a decrease in the temperature measurements.

In one aspect, the flow velocity is determined based on an integral of a waveform representative of the temperature measurements.

In one aspect, the flow velocity is determined based on a magnitude of noise in the temperature measurements. For example, increased noise can indicate faster flow velocities and decreased noise can indicate slower flow velocity.

In one aspect, the method also includes determining an injection zone of a subterranean well in which the fluid cable sensor assembly is inserted based on noise in the temperature measurements.

In one aspect, the method also includes inserting the fluid sensor cable assembly into a subterranean well to obtain the temperature measurements and the amount of one or more phases of the fluid flowing outside of the fluid sensor cable assembly at different depths within the subterranean well.

In one aspect, receiving the temperature measurements includes receiving reflections of light along the one or more optical cables from fiber Bragg grating reflectors disposed at the different locations along the length of the fluid cable assembly.

In one aspect, the distributed phase measurement signals represent amounts of two or more of water, gas, or oil at one or more different distances along the length of the core body.

In one embodiment, a fluid sensor system includes one or more fluid cable assemblies and a computer acquisition system. The one or more fluid sensor cable assemblies are configured to be disposed in one or more subterranean wells. The one or more fluid cable assemblies include an elongated internal core body and one or more optical cables extending along a length of the one or more fluid sensor cable assemblies and having temperature sensitive elements. The one or more cable assemblies also include one or more conductive coils wrapped around the core body along the length of the one or more fluid sensor cable assemblies. The computer acquisition system is configured to be operatively coupled with the one or more fluid sensor cable assemblies. The computer acquisition system is configured to conduct, for at least one of the fluid sensor cable assemblies, a distributed phase interrogation signal along the one or more conductive coils and is configured to receive distributed phase measurement signals conducted along the one or more conductive coils in response to conducting the interrogation signal. The distributed phase measurement signals are reflected back along the one or more conductive coils at different locations along the length of the fluid sensor cable assembly and represent amounts of different phases of the fluid at the different locations. The computer acquisition system also is configured to heat the at least one fluid sensor cable assembly by conducting a heating current along at least one of the conductive coils and, subsequent to heating the at least one fluid sensor cable assembly, to receive temperature measurements from the temperature sensitive elements at the different locations along the length of the at least one fluid sensor cable assembly, the temperature measurements representative of heat flux out of the fluid sensor cable assembly.

In one aspect, the computer acquisition system is configured to determine flow velocities of the fluid at the different locations along the length of the at least one fluid sensor cable assembly based on the temperature measurements.

In one aspect, the flow velocities are determined based on a change in a peak temperature of the temperature measurements subsequent to conducting the heating current.

In one aspect, the flow velocities are determined based on a duration of a decrease in the temperature measurements.

In one aspect, the flow velocities are determined based on an integral of a waveform representative of the temperature measurements.

In one aspect, the computer acquisition system is configured to be operatively coupled with two or more of the fluid sensor cable assemblies disposed in two or more of the subterranean wells. The computer acquisition system also is configured to concurrently determine amounts of two or more of water, gas, or oil at different depths in the two or more subterranean wells based on the distributed phase measurement signals.

In one aspect, the computer acquisition system is configured to be operatively coupled with two or more of the fluid sensor cable assemblies disposed in two or more of the subterranean wells. The computer acquisition system also can be configured to concurrently determine flow velocities of one or more fluids at different depths in the two or more subterranean wells based on the temperatures that are measured.

In one aspect, the computer acquisition system is configured to be operatively coupled with two or more of the fluid sensor cable assemblies disposed in two or more of the subterranean wells. The computer acquisition system also is configured to concurrently determine amounts of two or more of water, gas, or oil at different depths in the two or more subterranean wells based on the distributed phase measurement signals and to concurrently determine flow velocities of the two or more of water, gas, or oil at different depths in the two or more subterranean wells based on the temperatures that are measured.

In one aspect, the computer acquisition system is configured to generate an output signal to a display device that visually presents an image representative of the amounts and the flow velocities of the two or more of water, gas, or oil at the different depths in the two or more subterranean wells.

In one aspect, the computer acquisition system is configured to determine injection zones in one or more wells and fluid flow between one or more wells in which the one or more fluid sensor cable assemblies are located based on noise in the temperature measurements.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "an embodiment" or "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

As used herein, a structure, limitation, or element that is "configured to" perform a task or operation is particularly structurally formed, constructed, programmed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, programming of the structure or element to perform the corresponding task or operation in a manner that is different from an "off-the-shelf" structure or element that is not programmed to perform the task or operation, and/or denotes structural requirements of any structure, limitation, or element that is described as being "configured to" perform the task or operation.

What is claimed is:

1. A fluid sensor cable assembly comprising:
an internal core body having a length that is elongated from a first end to an opposite second end;
a coating disposed around the internal core body;
one or more conductive bodies extending along the length of the internal core body, the one or more conductive bodies configured to conduct an interrogation signal along the length of the internal core body, each of the one or more conductive bodies configured to conduct a heating current along the length of the internal core body to heat the fluid sensor cable assembly and conduct reflections of the interrogation signal as distributed phase measurement signals to a computer acquisition system;
one or more slots formed in the coating; and
one or more optical fibers extending along the length of the internal core body at a designated radial distance from a center axis of the internal core body, wherein the one or more optical fibers are disposed within the one or more slots, and wherein the one or more optical fibers including a plurality of temperature sensitive elements disposed at different locations along the length of the internal core body, the temperature sensitive elements configured to measure heat flux out of the fluid sensor cable assembly at the different locations along the length of the internal core body subsequent to heating the fluid sensor cable assembly by the one or more conductive bodies and communicate the heat flux that is measured via one or more optical fibers to the computer acquisition system.

2. The cable assembly of claim 1, wherein the one or more optical fibers are disposed within a dielectric tube with a hydrogen scavenging gel or coated with one or more of carbon or a metal.

3. The cable assembly of claim 1, wherein the temperature sensitive elements include fiber Bragg grating reflectors embedded within the one or more optical fibers.

4. The cable assembly of claim 1, wherein the distributed phase measurement signals represent amounts of two or more of water, gas, or oil at one or more different distances along the length of the internal core body.

5. The cable assembly of claim 1, wherein the heat flux that is measured at the different locations represents flow velocities of one or more fluids at the different locations along the length of the internal core body outside of the cable assembly.

6. The cable assembly of claim 1, wherein the one or more conductive bodies include a single conductive coil helically wound around the internal core body that conducts the heating current and conducts the distributed phase measurement signals.

7. The cable assembly of claim 1, further comprising a protective layer disposed outside of the one or more conductive bodies, the coating, and the one or more optical fibers.

8. A method comprising:
conducting a distributed phase interrogation signal along one or more conductive bodies extending along an elongated core body of a fluid sensor cable assembly, wherein a coating is disposed around the elongated core body, and wherein one or more slots are formed in the coating;
receiving distributed phase measurement signals along the one or more conductive bodies in response to conducting the interrogation signal, wherein the distributed phase measurement signals are reflected back along a conductive coil at different locations along a length of the fluid sensor cable assembly and represent an amount of one or more phases of a fluid flowing outside of the fluid sensor cable assembly;
heating the fluid sensor cable assembly by conducting a heating current for a designated period of time along the one or more of the conductive bodies; and
subsequent to heating the fluid sensor cable assembly, receiving temperature measurements from temperature sensitive elements in one or more optical fibers of the fluid sensor cable assembly at different locations along the length of the fluid sensor cable assembly, the temperature measurements representative of heat flux out of the fluid sensor cable assembly at the different locations, wherein the one or more optical fibers are disposed within the one or more slots, and wherein each of the one or more conductive bodies is configured to conduct the heating current and the distributed phase measurement signals.

9. The method of claim 8, wherein heating the fluid sensor cable assembly includes alternating between conducting the heating current during a first time period and stopping conduction of the heating current for a subsequent, second time period during one or more heating iterations.

10. The method of claim 8, further comprising determining a flow velocity of one or more fluids outside of the fluid sensor cable assembly based on the temperature measurements.

11. The method of claim 10, wherein the flow velocity is determined based on one or more of a duration of a decrease in the temperature measurements, an integral of a waveform representative of the temperature measurements, or a magnitude of noise in the temperature measurements.

12. The method of claim 10, further comprising determining an injection zone of a subterranean well in which the fluid cable sensor assembly is inserted based on noise in the temperature measurements.

13. The method of claim 8, further comprising inserting the fluid sensor cable assembly into a subterranean well to obtain the temperature measurements and the amount of one or more phases of the fluid flowing outside of the fluid sensor cable assembly at different depths within the subterranean well.

14. The method of claim 8, wherein receiving the temperature measurements includes receiving reflections of light along the one or more optical fibers from fiber Bragg grating reflectors disposed at the different locations along the length of the fluid sensor cable assembly.

15. The method of claim 8, wherein the distributed phase measurement signals represent amounts of two or more of water, gas, or oil at one or more different distances along the length of the elongated core body.

16. A fluid sensor system comprising:
one or more fluid sensor cable assemblies configured to be disposed in one or more subterranean wells, the one or more fluid sensor cable assemblies including an elongated internal core body, a coating disposed around the elongated internal core body, one or more slots formed in the coating, one or more optical fibers extending along a length of the one or more fluid sensor cable assemblies and having temperature sensitive elements, one or more conductive coils wrapped around the elongated internal core body along the length of the one or more fluid sensor cable assemblies, wherein the one or more optical fibers are disposed within the one or more slots; and
a computer acquisition system configured to be operatively coupled with the one or more fluid sensor cable assemblies, the computer acquisition system configured to conduct, for at least one of the fluid sensor cable assemblies, a distributed phase interrogation signal along the one or more conductive coils and to receive distributed phase measurement signals conducted along the one or more conductive coils in response to conducting the interrogation signal, wherein the distributed phase measurement signals are reflected back along the one or more conductive coils at different locations along the length of the fluid sensor cable assembly and represent amounts of different phases of a fluid at the different locations,
wherein the computer acquisition system also is configured to heat at least one fluid sensor cable assembly by conducting a heating current along at least one of the conductive coils and, subsequent to heating the at least one fluid sensor cable assembly, to receive temperature measurements from the temperature sensitive elements at the different locations along the length of the at least one fluid sensor cable assembly, the temperature measurements representative of heat flux out of the fluid sensor cable assembly, and wherein each of the one or more conductive coils is configured to conduct the heating current and the distributed phase measurement signals.

17. The system of claim 16, wherein the computer acquisition system is configured to determine flow velocities of the fluid at the different locations along the length of the at least one fluid sensor cable assembly based on the temperature measurements.

18. The system of claim 17, wherein the flow velocities are determined based on one or more of a change in a peak temperature of the temperature measurements subsequent to conducting the heating current, a duration of a decrease in the temperature measurements, or an integral of a waveform representative of the temperature measurements.

19. The system of claim 16, wherein the computer acquisition system is configured to be operatively coupled with two or more of the fluid sensor cable assemblies disposed in two or more subterranean wells, the computer acquisition system also configured to one or more of concurrently determine amounts of two or more of water, gas, or oil at different depths in the two or more subterranean wells based on the distributed phase measurement signals or concurrently determine flow velocities of one or more fluids at the different depths in the two or more subterranean wells based on the temperatures that are measured.

20. The system of claim 16, wherein the computer acquisition system is configured to determine injection zones in one or more wells and fluid flow between the one or more wells in which the one or more fluid sensor cable assemblies are located based on noise in the temperature measurements.

* * * * *